(12) United States Patent  
Henley et al.

(10) Patent No.: US 6,735,470 B2  
(45) Date of Patent: May 11, 2004

(54) ELECTROKINETIC DELIVERY OF MEDICAMENTS

(75) Inventors: Julian L. Henley, New Haven, CT (US); Kuo Wei Chang, Waltham, MA (US); Joseph Potter, Oak Bluffs, MA (US); Dennis I. Goldberg, Boston, MA (US); Christopher H. Porter, Woodinville, WA (US); V. Lorenzo Porcelli, Ossining, NY (US)

(73) Assignee: BioPhoretic Therapeutic Systems, LLC, Framingham, MA (US)

( * ) Notice: Subject to any disclaimer, the term of this patent is extended or adjusted under 35 U.S.C. 154(b) by 3 days.

(21) Appl. No.: 10/245,337

(22) Filed: Sep. 18, 2002

(65) Prior Publication Data

US 2003/0018295 A1 Jan. 23, 2003

Related U.S. Application Data

(62) Division of application No. 09/584,138, filed on May 31, 2000.

(51) Int. Cl.⁷ .................................................. A61N 1/30
(52) U.S. Cl. ........................ 604/20; 604/22; 604/501; 601/1
(58) Field of Search .............. 604/20, 22, 19, 604/289, 500, 501; 607/115, 120, 149, 152, 98; 601/1, 2; 128/898

(56) References Cited

U.S. PATENT DOCUMENTS

| 206,474 A | 7/1878 | Morel |
| 279,524 A | 6/1883 | Beaty .................... 607/145 |
| 484,522 A | 10/1892 | McBride |
| 600,290 A | 3/1898 | Muir |
| 1,967,927 A | 7/1934 | Deustch .................... 604/20 |
| 2,047,308 A | 7/1936 | Chapman .................... 128/799 |

(List continued on next page.)

FOREIGN PATENT DOCUMENTS

| AT | 0232642 | 3/1964 | .............. 604/20 |
| EP | 0230749 | 8/1987 | .............. 604/20 |
| EP | 0309093 A1 | 3/1989 | .............. 604/20 |
| EP | 617979 A1 | 10/1994 | |
| FR | 1445703 | 6/1966 | .............. 604/20 |
| FR | 2 513 129 | 3/1983 | |
| GB | 0299533 | 11/1928 | .............. 604/20 |
| JP | 3-170172 | 7/1991 | |
| SU | 654254 | 3/1979 | |
| SU | 931191 | 5/1982 | |
| SU | 1003853 | 3/1983 | |
| WO | 07269 | 12/1986 | .............. 604/20 |
| WO | WO 90/06153 | 6/1990 | |
| WO | 08571 | 8/1990 | .............. 604/20 |
| WO | 03790 | 3/1993 | .............. 604/20 |

OTHER PUBLICATIONS

"Iontophoretic Treatment of Oral Herpes," Henley et al.; Laryngoscope, vol. 94, No. 1, pp. 118–121, Jan. 1984.

(List continued on next page.)

Primary Examiner—Henry Bennett
Assistant Examiner—Fadi H. Dahbour
(74) Attorney, Agent, or Firm—Nixon & Vanderhye P.C.

(57) ABSTRACT

An electrokinetic delivery or diagnostic device for personal use and self-administration of a medicament to a treatment site is provided. The device includes a housing containing a power supply, a first active electrode and a ground tactile electrode. An applicator includes a pad for containing medicament for overlying the first electrode of the device. The medicament may be applied by the user to the pad, contained within the pad or contained in rupturable capsules within the pad, together with a hydrogel if necessary for imparting electrical conductivity whereby, upon application of the applicator to the treatment site, the medicament is electrokinetically transported into the treatment site. In another form, the applicator is self-contained, having a power supply, a first electrode overlying a pad and a ground electrode from the opposite side from the pad whereby the individual presses the pad against the treatment site to complete the electrical circuit and electrokinetically drive the medicament into the treatment site.

50 Claims, 15 Drawing Sheets

U.S. PATENT DOCUMENTS

| | | | | |
|---|---|---|---|---|
| 2,123,980 | A | 7/1938 | Warwick | |
| 2,126,070 | A | 8/1938 | Wappler | |
| 2,834,344 | A | 5/1958 | Kanai | |
| 3,019,787 | A | 2/1962 | Simmons | |
| 3,048,170 | A | 8/1962 | Lemos | |
| 3,107,672 | A | 10/1963 | Hofmann | |
| 3,163,166 | A | 12/1964 | Brant et al. | |
| 3,298,368 | A | 1/1967 | Charos | 128/260 |
| 3,520,297 | A | 7/1970 | Bechtold | |
| 3,556,105 | A | 1/1971 | Shepard | |
| 3,645,260 | A | 2/1972 | Cinotti et al. | |
| 3,716,054 | A | 2/1973 | Porter et al. | |
| 3,831,598 | A | 8/1974 | Tice | |
| 3,848,600 | A | 11/1974 | Patrick, Jr. et al. | 128/783 |
| 4,116,238 | A | 9/1978 | Pettijohn | 128/172.1 |
| 4,211,222 | A | 7/1980 | Tapper | 128/803 |
| 4,292,968 | A | 10/1981 | Ellis | 128/207.21 |
| 4,301,794 | A | 11/1981 | Tapper | 604/20 |
| 4,325,367 | A | 4/1982 | Tapper | |
| 4,383,529 | A | 5/1983 | Webster | |
| 4,393,884 | A | 7/1983 | Jacobs | 131/273 |
| 4,406,658 | A | 9/1983 | Lattin et al. | 604/20 |
| 4,416,274 | A | 11/1983 | Jacobsen et al. | 128/803 |
| 4,429,703 | A | 2/1984 | Haber | 131/273 |
| 4,474,570 | A | 10/1984 | Ariura et al. | 604/20 |
| 4,510,939 | A | 4/1985 | Brenman et al. | 128/639 |
| 4,639,244 | A | 1/1987 | Rizk et al. | |
| 4,655,229 | A | 4/1987 | Sensabaugh, Jr. et al. | 131/273 |
| 4,665,921 | A | 5/1987 | Teranishi et al. | |
| 4,689,039 | A | 8/1987 | Masaki | |
| 4,702,732 | A | 10/1987 | Powers et al. | |
| 4,708,716 | A | 11/1987 | Sibalis | 604/20 |
| 4,735,217 | A | 4/1988 | Gerth et al. | 131/273 |
| 4,747,819 | A | 5/1988 | Phipps et al. | |
| 4,756,318 | A | 7/1988 | Clearman et al. | 131/359 |
| 4,763,660 | A | 8/1988 | Kroll et al. | 128/798 |
| 4,764,164 | A | 8/1988 | Sasaki | 604/20 |
| 4,767,402 | A | 8/1988 | Kost et al. | |
| 4,771,796 | A | 9/1988 | Myer | 131/273 |
| 4,776,353 | A | 10/1988 | Lilja et al. | 131/297 |
| 4,786,278 | A | 11/1988 | Masaki | 604/20 |
| 4,787,888 | A | 11/1988 | Fox | |
| 4,793,366 | A | 12/1988 | Hill | 131/273 |
| 4,800,903 | A | 1/1989 | Ray et al. | 131/273 |
| 4,808,152 | A | 2/1989 | Sibalis | 604/20 |
| 4,813,437 | A | 3/1989 | Ray | 131/273 |
| 4,820,263 | A | 4/1989 | Spevak et al. | 604/20 |
| 4,821,740 | A | 4/1989 | Tachibana et al. | 604/20 |
| 4,838,273 | A | 6/1989 | Cartmell | 600/392 |
| 4,865,582 | A | 9/1989 | Sibalis | 604/20 |
| 4,907,606 | A | 3/1990 | Lilja et al. | 131/273 |
| 4,913,148 | A | 4/1990 | Diethelm | |
| 4,917,119 | A | 4/1990 | Potter et al. | 131/273 |
| 4,919,648 | A | 4/1990 | Sibalis | 604/20 |
| 4,922,901 | A | 5/1990 | Brooks et al. | 128/203.26 |
| 4,931,046 | A | 6/1990 | Newman | 604/20 |
| 4,942,883 | A | 7/1990 | Newman | 604/20 |
| 4,950,229 | A | 8/1990 | Sage, Jr. | 604/20 |
| 4,953,565 | A | 9/1990 | Tachibana et al. | 604/20 |
| 4,957,480 | A | 9/1990 | Morenings | |
| 4,979,938 | A | 12/1990 | Stephen et al. | |
| 4,997,418 | A | 3/1991 | DeMartini | |
| 5,002,527 | A | 3/1991 | Reller et al. | |
| 5,006,108 | A | 4/1991 | LaPrade | 604/20 |
| 5,019,034 | A | 5/1991 | Weaver et al. | 604/20 |
| 5,037,381 | A | 8/1991 | Bock et al. | |
| 5,042,975 | A | 8/1991 | Chien et al. | |
| 5,047,007 | A | 9/1991 | McNichols et al. | 604/20 |
| 5,053,001 | A | 10/1991 | Reller et al. | 604/20 |
| 5,060,671 | A | 10/1991 | Counts et al. | 131/329 |
| 5,090,402 | A | 2/1992 | Bazin et al. | |
| 5,115,805 | A | 5/1992 | Bommannan et al. | |
| 5,133,352 | A | 7/1992 | Lathrop et al. | |
| 5,135,478 | A | 8/1992 | Sibalis | |
| 5,135,479 | A | 8/1992 | Sibalis et al. | 604/20 |
| 5,147,291 | A | 9/1992 | Cukier | 604/22 |
| 5,160,316 | A | 11/1992 | Henley | 604/20 |
| 5,162,042 | A | 11/1992 | Gyory et al. | |
| 5,167,242 | A | 12/1992 | Turner et al. | 131/273 |
| 5,169,384 | A | 12/1992 | Bosniak et al. | |
| 5,171,215 | A | 12/1992 | Flanagan | 604/20 |
| 5,203,768 | A | 4/1993 | Haak et al. | |
| 5,250,022 | A | 10/1993 | Chien et al. | |
| 5,254,081 | A | 10/1993 | Maurer et al. | 604/20 |
| 5,279,543 | A | 1/1994 | Glikfeld et al. | |
| 5,284,471 | A | 2/1994 | Sage, Jr. | |
| 5,298,017 | A | 3/1994 | Theeuwes et al. | |
| 5,310,404 | A | 5/1994 | Gyory et al. | |
| 5,312,326 | A | 5/1994 | Myers et al. | |
| 5,314,502 | A | 5/1994 | McNichols et al. | |
| 5,331,979 | A | 7/1994 | Henley | |
| 5,354,321 | A | 10/1994 | Berger | |
| 5,360,440 | A | 11/1994 | Andersen | |
| 5,362,307 | A | 11/1994 | Guy et al. | |
| 5,362,308 | A | 11/1994 | Chien et al. | |
| 5,374,241 | A | 12/1994 | Lloyd et al. | |
| 5,374,242 | A | 12/1994 | Haak et al. | |
| 5,376,107 | A | 12/1994 | Inagi et al. | |
| 5,391,195 | A | 2/1995 | Van Groningen | |
| 5,395,310 | A | 3/1995 | Untereker et al. | |
| 5,413,590 | A | 5/1995 | Williamson | |
| 5,415,629 | A | 5/1995 | Henley | |
| 5,421,816 | A | 6/1995 | Lipkovker | |
| 5,441,936 | A | 8/1995 | Houghten et al. | |
| 5,443,441 | A | 8/1995 | De Claviere | |
| 5,458,569 | A | 10/1995 | Kirk, III et al. | 604/20 |
| 5,464,387 | A | 11/1995 | Haak et al. | |
| 5,466,217 | A | 11/1995 | Myers et al. | |
| 5,470,349 | A | 11/1995 | Kleditsch et al. | |
| 5,494,679 | A | 2/1996 | Sage, Jr. et al. | |
| 5,501,705 | A | 3/1996 | Fakhri | |
| 5,514,167 | A | 5/1996 | Smith et al. | |
| 5,538,503 | A | 7/1996 | Henley | |
| 5,540,669 | A | 7/1996 | Sage, Jr. et al. | 604/20 |
| 5,551,953 | A | 9/1996 | Lattin et al. | |
| 5,558,632 | A | 9/1996 | Lloyd et al. | |
| 5,562,607 | A | 10/1996 | Gyory | |
| 5,589,563 | A | 12/1996 | Ward et al. | |
| 5,603,693 | A | 2/1997 | Frenkel et al. | |
| 5,607,461 | A | 3/1997 | Lathrop | |
| 5,607,691 | A | 3/1997 | Hale et al. | |
| 5,618,275 | A | 4/1997 | Bock | |
| 5,658,247 | A | 8/1997 | Henley | |
| 5,667,487 | A | 9/1997 | Henley | |
| 5,668,170 | A | 9/1997 | Gyory | |
| 5,676,648 | A | 10/1997 | Henley | |
| 5,678,273 | A | 10/1997 | Porcelli | |
| 5,688,233 | A | 11/1997 | Hofmann et al. | |
| 5,697,896 | A | 12/1997 | McNichols et al. | |
| 5,700,457 | A | 12/1997 | Dixon | |
| 5,711,761 | A | 1/1998 | Untereker et al. | |
| 5,713,846 | A | 2/1998 | Bernhard et al. | |
| 5,722,397 | A | 3/1998 | Eppstein | |
| 5,725,817 | A | 3/1998 | Milder | |
| 5,733,255 | A | 3/1998 | Dinh et al. | |
| 5,755,750 | A | 5/1998 | Petruska et al. | |
| 5,788,666 | A | 8/1998 | Atanasoska | |
| 5,794,774 | A | 8/1998 | Porcelli | |
| 5,795,321 | A | 8/1998 | McArthur et al. | |
| 5,797,867 | A | 8/1998 | Guerrara et al. | |
| 5,830,175 | A | 11/1998 | Flower | |

| | | |
|---|---|---|
| 5,840,057 A | 11/1998 | Aloisi |
| 5,846,217 A | 12/1998 | Beck et al. |
| 5,865,786 A | 2/1999 | Sibalis et al. ............... 604/20 |
| 5,879,323 A | 3/1999 | Henley |
| 5,882,676 A | 3/1999 | Lee et al. |
| 5,899,875 A | 5/1999 | Millot |
| 5,899,876 A | 5/1999 | Flower ..................... 604/20 |
| 5,908,401 A | 6/1999 | Henley ..................... 604/20 |
| 5,911,319 A | 6/1999 | Porcelli et al. |
| 5,919,155 A | 7/1999 | Lattin et al. ................ 604/20 |
| 5,931,859 A | 8/1999 | Burke |
| 5,935,598 A | 8/1999 | Sage et al. |
| 5,954,684 A | 9/1999 | Flower et al. .............. 604/20 |
| 5,961,482 A | 10/1999 | Chien et al. |
| 5,961,483 A | 10/1999 | Sage et al. |
| 5,968,005 A | 10/1999 | Tu |
| 5,968,006 A | 10/1999 | Hofmann |
| 5,983,130 A | 11/1999 | Phipps et al. |
| 6,004,309 A | 12/1999 | Phipps |
| 6,004,547 A | 12/1999 | Rowe et al. |
| 6,006,130 A | 12/1999 | Higo et al. |
| 6,018,679 A | 1/2000 | Dinh et al. |
| 6,023,639 A | 2/2000 | Hakky et al. |
| 6,032,073 A | 2/2000 | Effenhauser |
| 6,038,485 A | 3/2000 | Axelgaard |
| 6,041,252 A | 3/2000 | Walker et al. |
| 6,041,253 A | 3/2000 | Kost et al. |
| 6,048,545 A | 4/2000 | Keller et al. |
| 6,057,374 A | 5/2000 | Huntington et al. |
| 6,101,411 A | 8/2000 | Newsome |
| 6,148,231 A | 11/2000 | Henley ..................... 604/20 |
| 6,148,232 A | 11/2000 | Avrahami .................. 604/20 |
| 6,167,302 A | 12/2000 | Millot |
| 6,385,487 B1 | 5/2002 | Henley ..................... 604/20 |
| 6,477,410 B1 | 11/2002 | Henley et al. |
| RE38,000 E * | 2/2003 | Henley ..................... 604/20 |
| 6,553,253 B1 * | 4/2003 | Chang ...................... 604/20 |
| RE38,341 E * | 12/2003 | Henley ..................... 604/20 |

OTHER PUBLICATIONS

"Iontophoretic Application of Idoxuridine for Recurrent Herpes Labialis: Report of Preliminary Chemical Trials," Gangarosa et al.; Meth. And Find. Exptl. Clin. Pharmacol. 1(2), pp. 105–109 (1979).

"Iontophoretic of Vidarabine Monophosphate for Herpes Orolabialis," Gangarosa et al.; The Journal of Infectious Diseases, vol. 154, No. 6, pp. 930–934, Dec. 1986.

"The Natural History of Recurrent Herpes Simplex Labialis," Spruance et al.; The New England Journal of Medicine, vol. 297, No. 2, pp. 69–75, Jul. 14, 1977.

"Infection with Herpes–Simplex Viruses 1 and 2," Nahmias et al.; The New England Journal of Medicine, pp. 667–674, Sep. 27, 1973.

"Anesthesia of the Human Tympanic Membrane by Iontophoresis of a Local Anesthetic," Comeau et al.; The Laryngoscope, 88:1978, pp. 277–285.

"Iontophoretic Application of Drugs," Waud, J. Appl. Physiol. 23(1), 1967, pp. 128–130.

"Antibiotic Iontophoresis in the Treatment of Ear Chondritis," LaForest et al., Physical Therapy, vol. 58, No. 1, Jan. 1978, pp. 32–34.

"The Quantity and Distribution of Radiolabeled Dexamethasone Delivered to Tissue by Iontophoresis," Glass et al.; International Journal of Dermatology, vol. 19, Nov. 1980, pp. 519–525.

"Iontophoretic Application of Antiviral Chemotherapeutic Agents," Hill et al., Annals New York Academy of Sciences, pp. 604–612.

"Ocular Iontophoresis," Hill et al. Paper, Louisiana State University Medical Center, School of Medicine, New Orleans, Louisiana, pp. 331–354.

"Iontophoretic Application of Adenine Arabinoside Monophosphate to Herpes Simplex Virus Type 1–Infected Hairless Mouse Skin," Park et al.; Antimicrobial Agents and Chemotherapy, vol. 14, No. 4, Oct., 1978, pp. 605–608.

"Iontophoresis: Applications in Transdermal Medication Delivery," Costello et al.; Physical Therapy, vol. 75, No. 6, pp. 104/554–113/113/563, Jun. 1995.

Physical Enhancement of Dermatologic Drug Delivery: Iontophoresis and Phonophoresis, Kassan et al., Journal of the American Academy of Dermatology, Apr. 1996, pp. 657–666.

"Iontophoresis and Herpes Labialis," Boxhall et al.; The Medical Journal of Australia, May 26, 1984, pp. 686–687.

"Iontophoresis: A Method of Antibiotic Administration in the Burn Patient," Rapperport et al., Plastic and Reconstructive Surgery, 1965, vol. 36, No. 5, pp. 547–552.

"Iontophoresis for Enhancing Penetration of Dermatologic and Antiviral Drugs," Gangarosa et al., Journal of Dermatology, vol. 22, No. 11, pp. 865–875, Nov. 1995.

"Iontophoretic Treatment of Herpetic Whitlow," Gangarosa et al., Arch. Phys. Med. Rehabil., vol. 70, pp. 336–340 Apr. 1989.

"Iontophoretic Application of Antiviral Drugs," Gangarosa et al., Proceedings of an International Symposium held in Tokushima City, Japan, pp. 201–204, Jul. 27–30, 1981.

"Iontophoretic Application of Adenine Arabinoside Monophosphate for the Treatment of Herpes Simplex Virus Type 2 Skin Infections in Hairless Mice," Gangarosa The Journal of Infectious Diseases, vol. 140, No. 6, pp. 1014, Dec. 1979.

"Effect of Iontophoretic and Topical Application of Antiviral Agents in Treatment of Experimetnal HSV–1 Keratitis in Rabbits," Kwon et al., Investigative Ophthalmology & Visual Science, vol. 18, No. 9, pp. 984–988, Sep., 1979.

"Acyclovir and Vidarabine Monophosphate: Comparison of Iontophoretic and Intravenous Administration for the Treatment of HSV–1 Stromal Keratitis," Hill et al., The American Journal of Medicine, Acyclovir Symposium, pp. 300–304.

"Thymine Arabinoside (Ara–T) Topical and Iontophoretic Applications for Herpes Simplex Virus Type 1 and Type 2 Skin Infections in Hairless Mice," Hill et al., Meth. And Find. Exptl. Clin. Pharmacol. 6(1), pp. 17–20, 1984.

"Iontophoresis Enhances the Transport of Acyclovir Through Nude Mouse Skin by Electrorepulsion and Electroosmosis," Volpato et al., Pharmaceutical Research, vol. 12, No. 11, pp. 1623–1627, 1995.

"Early Application of Topical 15% Idoxuridine n Dimethyl Sulfoxide Shortens the Course of Herpes Simplex Labialis: A Multicenter Placebo–Controlled Trial," Spruance et al., The Journal of Infectious Diseases, 1990; vol. 161; pp. 191–197.

"Iontophoresis for Surface Local Anesthesia," Gangarosa, JADA, vol. 88, pp. 125–128, Jan. 1974.

"Conductivity of Drugs Used for Iontophoresis," Gangarosa et al., Journal of Pharmaceutical Sciences, vol. 67, No. 10, pp. 1439–1443, Oct. 1978.

"A Pilot Study of Iontophoretic Cisplatin Chemotherapy of Basal and Squamous Cell Carcinomas of the Skin," Chang et al., Arch. Dermatol., vol. 129, pp. 425–427, Apr. 1993.

"How Modern Iontophoresis Can Improve Your Practice," Gangarosa et al., (Quintessence International) Oral Surgery, No. 10, Report 2135, Oct. 1982, pp. 1027–1038.

"Postherpetic Neuralgia," Baron et al., Brain (1993), 116, pp. 1477–1496.

"Iontophoretic Assistance of 5–Iodo–2'–Deoxyuridine Penetration into Neonatal Mouse Skin and Effects of DNA Synthesis," Gangarosa et al., Society for Experimental Biology and Medicine, pp. 439–443, 1997.

"Electrophoretic Evaluation of the Mobility of Drugs Suitable for Iontophoresis," Kamath et al., Meth. Find. Exp. Clin. Pharmacol., 1995, 17(4): pp. 227–232.

"Transdermal Drug Delivery by Passive Diffusion and Iontophoresis: A Review," Singh et al., Medicinal Research Reviews, vol. 13, No. 5, 1993, pp. 569–621.

"Iontophoresis: Electrorepulsion and Electroosmosis," Guy et al., Journal of Controlled Release 64 (2000) 129–132.

"Treatment of Common Cutaneous Herpes Simplex Virus Infections," Emmert, American Family Physician, vol. 61, No. 6, Mar. 15, 2000, pp. 1697–1704.

"Gelatin–stabilised Microemulsion–Based Oranogels: Rheology and Application in Iontophoretic Transdermal Drug Delivery," Kantaria et al., Journal of Controlled Release 60 (1999) 355–365.

"Electrorepulsion Versus Electroosmosis: Effect of pH on the Iontophoretic Flux of 5–Fluorouracil," Merino et al., Pharmaceutical Research, vol. 16, No. 6 (1999).

"Azelaic Acid: Potential as a General Antitumoural Agent," Breathnach, Medical Hypotheses (1999) 52(3) 221–226.

"Treatment of Mucocutaneous Herpes Simplex Virus Infections Unresponsive to Acyclovir with Topical Foscarnet Cream in AIDS Patients: A Phase I/II Study," Javaly et al., Journal of Acquired Immune Deficiency Syndromes 21:301–306.

"Efficacy and Safety of Azelaic Acid and Glycolic Acid Combination Therapy Compared with Tretinoin Therapy for Acne," Spellman et al., Clinical Therapeutics, vol. 20, No. 4, 1998, pp. 711–721.

"Passive Versus Electrotransport–Facilitated Transdermal Absorption of Ketorolac," Park et al., Clinical Pharmacology & Therapeutics, vol. 63, No. 3, pp. 303–315.

"Soriudine Versus Acyclovir for Treatment of Dermatomal Herpes Zoster in Human Immunodeficiency Virus–Infected Patients: Results from a Randomized, Controlled Clinical Trial," Gnann et al., Antimicrobial Agents and Chemotherapy, vol. 42, No. 5, May 1998, pp. 1139–1145.

"Azelaic Acid 20% Cream (AZELEX®) and the Medical Management of Acne Vulgaris," Gibson, Dermatology Nursing, vol. 9, No. 5, pp. 339–344.

"Sorivudine: A Promising Drug for the Treatment of Varicella–Zoster Virus Infection," Whitley, Neurology 1995; 45 (Supp. 8), pp. S73–S75.

"Antiherpesviral and Anticellular Effects of 1–β–D–Arabinofuranosyl–E–5–(2–Halogenovinyl) Uracils," Machida et al., Antimicrobial Agents and Chemotherapy, Jul. 1981, pp. 47–52.

"Herpes Simplex," American Academy of Dermatology, 1987, Revised 1991, 1993.

"'Common Cold' Virus is Near," Haney, The Associated Press, Jan. 15, 2000.

"New Medicines Move to Eradicate Acne," Hemphill, The New York Times, Feb. 29, 2000.

"Warts," American Academy of Dermatology, American Academy of Dermatology, 1997, Revised 1991, 1993.

"Psoriasis," American Acadmey of Dermatology, 1994.

"Eczema/Atopic Dermatitis," American Academy of Dermatology, 1987, Revised 1991, 1993, 1995.

"Skin Cancer: An Undeclared Epidemic," American Academy of Dermatology, 1988, Revised 1989, 1993, 1994.

* cited by examiner

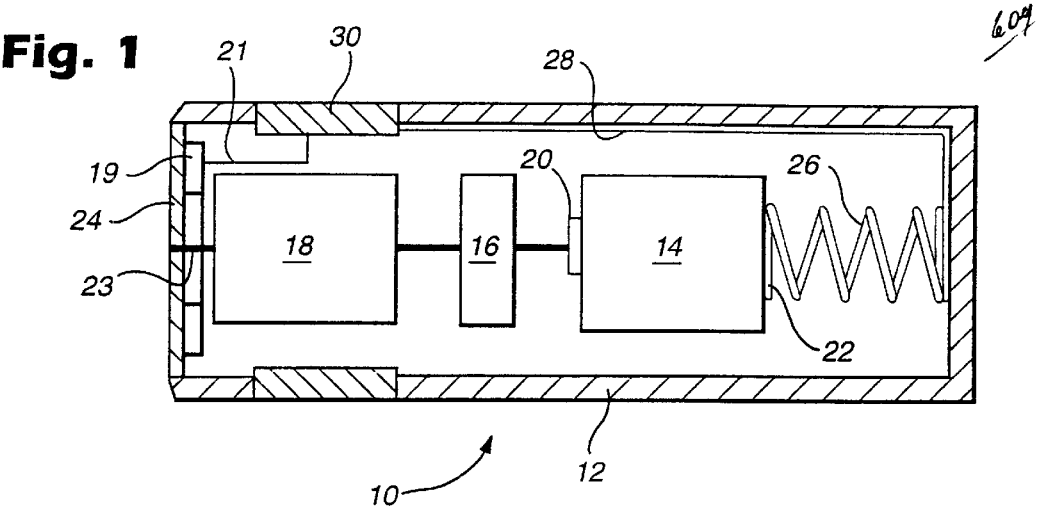
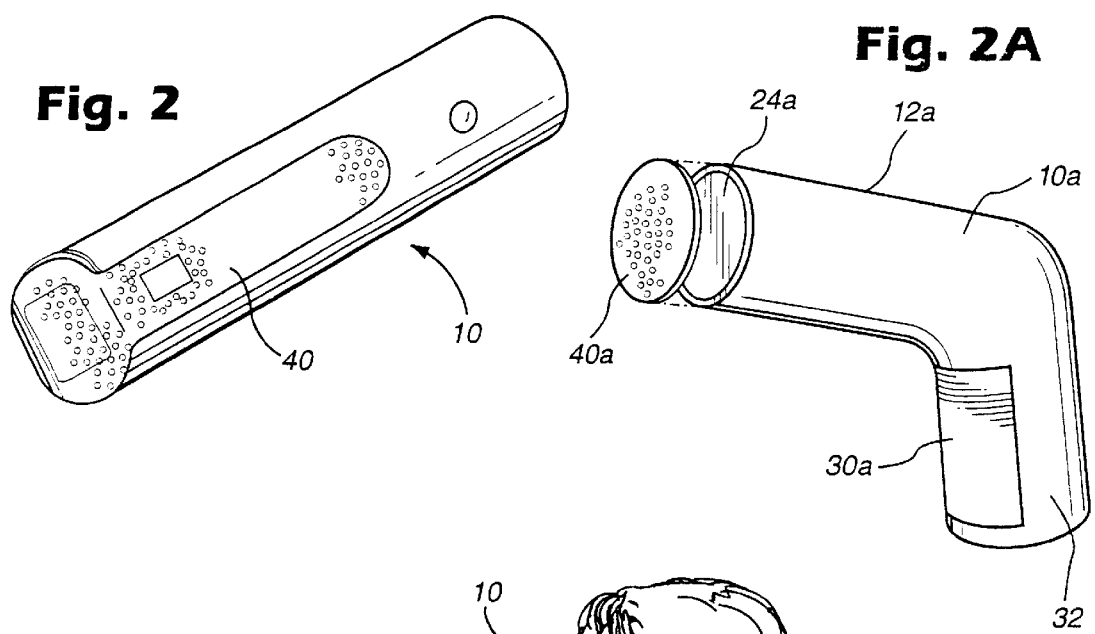

Fig. 9
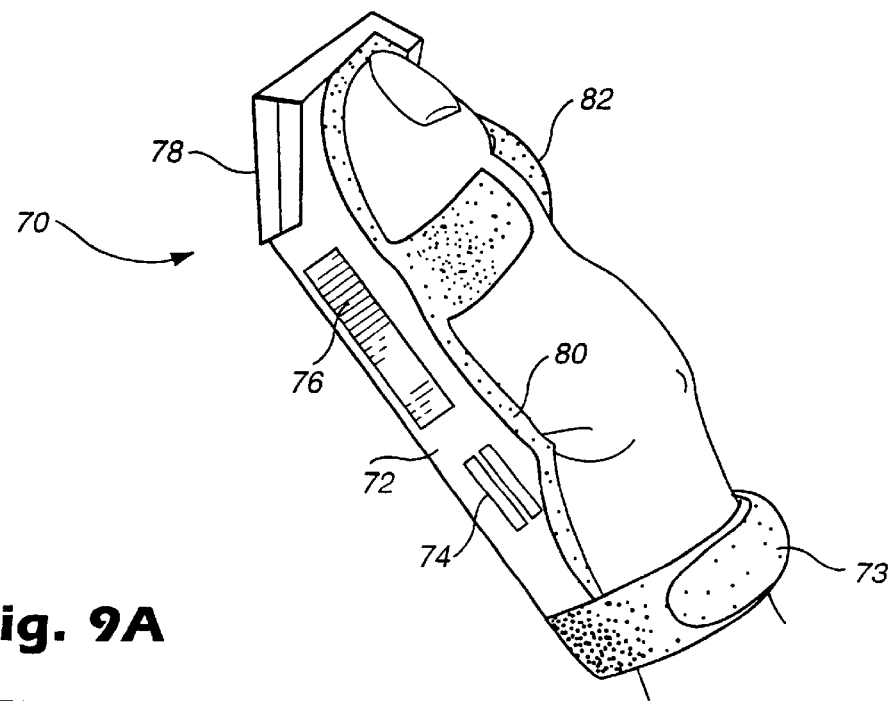
Fig. 9A
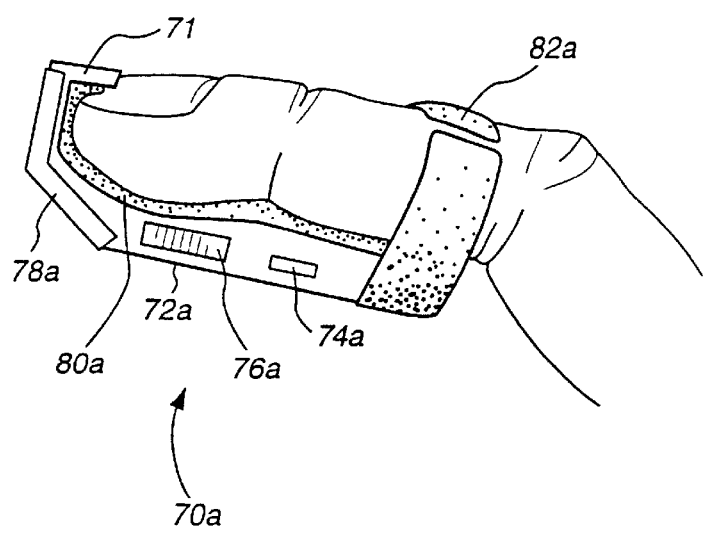
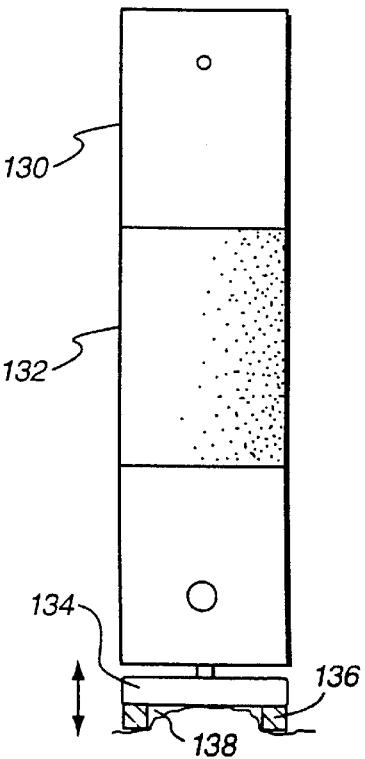
Fig. 15

Fig. 27
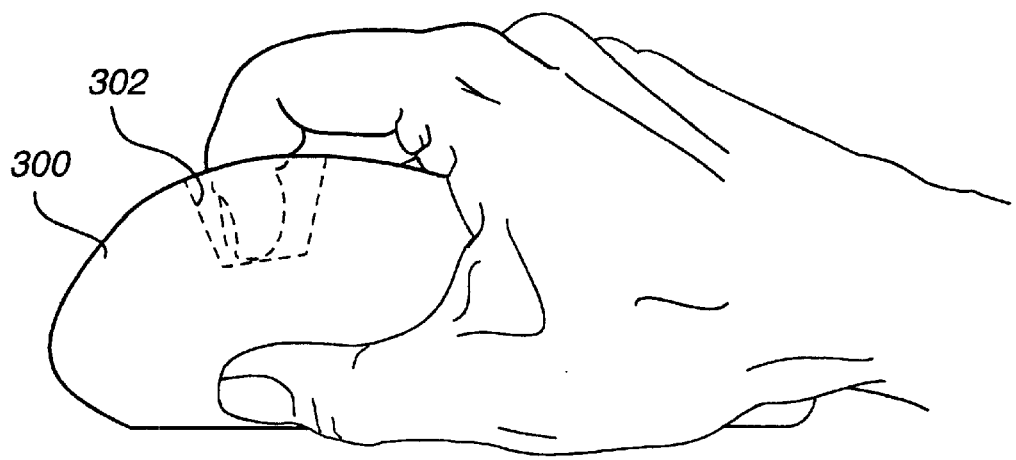
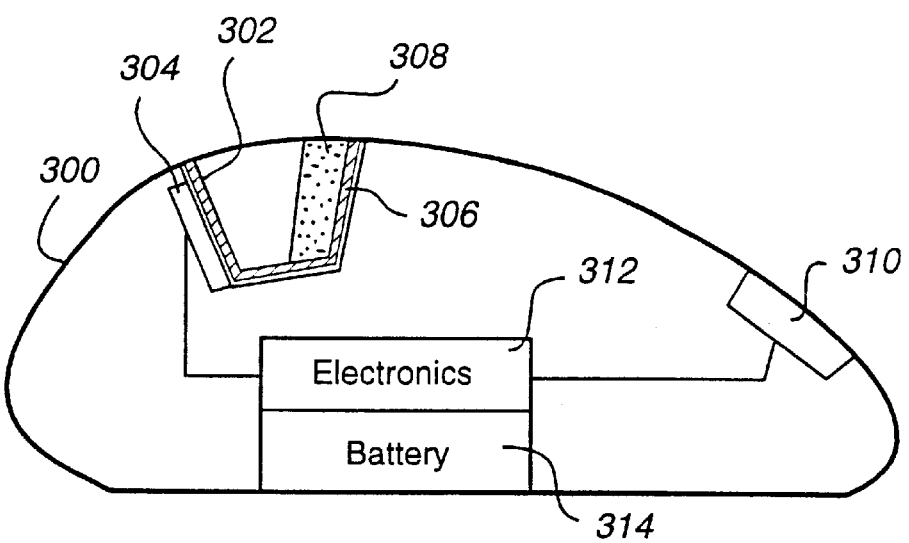
Fig. 28

ELECTROKINETIC DELIVERY OF MEDICAMENTS

RELATED APPLICATIONS

This application is a divisional of application Ser. No. 09/584,138, filed May 31, 2000, of common assignee herewith, the entire content of which is incorporated herein by reference.

BACKGROUND OF THE INVENTION

The present invention relates generally to the electrokinetic mass transfer of substances into and/or extracting substances from tissue and particularly to apparatus and methods for extracting, containing and/or delivering substance, e.g., a medicament to a treatment site.

Electrokinetic delivery of medicaments for applying medication locally through an individual's skin is known. One type of electrokinetic delivery mechanism is iontophoresis, i.e., the application of an electric field to the skin to enhance the skin's permeability and to deliver various ionic agents, e.g., ions of soluble salts or other drugs. In certain situations, iontophoretic transdermal or transmucocutaneous delivery techniques have obviated the need for hypodermic injection for many medicaments, thereby eliminating the concomitant problem of trauma, pain and risk of infection to the individual. Other types of electrokinetic delivery mechanisms include electroosmosis, electroporation, electromigration, electrophoresis and endosmose, any or all of which are generally known as electrotransport, electromolecular transport or iontophoretic methods. The electrokinetic delivery mechanism may also be accompanied by ultrasonic vibration to further facilitate electrokinetic transport of the substance, e.g., by opening pores in the skin. Ultrasound may be employed in a number of ways such as (i) traditional piezoelectric elements, (ii) Application Specific Integrated Circuits (ASIC) with ultrasound transmitter built in or (iii) by thin foil sheets with incorporated piezoelectric dipole elements.

There are several difficulties with electrokinetic delivery of substances such as medicaments. One is the heretofore need for somewhat cumbersome, bulky and costly equipment which oftentimes requires the presence of an individual at a doctor's office or treatment center and use of medical professionals to administer the medicament. Private, self-administration of medicaments or for diagnostic application by the individual at non-medical or non-professional facilities is highly desirable. Also, an easily transportable apparatus for electrokinetic delivery of medication, for example, a lightweight, compact portable device useful with an applicator packaged as a single or unit dosage applicator, appears ideal as a patient/consumer friendly self-administration system appropriate for many circumstances.

BRIEF DESCRIPTION OF THE INVENTION

In accordance with a preferred embodiment of the present invention, there is provided a portable, self-contained, hand-held lightweight, compact and wireless electrokinetic device for delivering or removing a substance, e.g., a medicament, and a unit dosage substance applicator for use with the device for the self-administration of a medicament to the skin. By the term substance is meant a medicament as well as natural or homeopathic products that may be outside the definition of medicament, e.g., inks and pigments for tattoos, and more generally includes any substance capable of electrokinetic transport through skin or mucocutaneous membrane, e.g., into a treatment site or from a site, e.g., for diagnostic purposes. The majority of applications using the present invention are for applying medicaments to treatment sites and therefore the term medicament is used in lieu of the term substance throughout this specification. By medicament is meant any chemical or biologic that may be used on or administered to humans or animals as an aid in the diagnosis, treatment or prevention of disease or other abnormal or cosmetic condition or for the relief of pain or to control, diagnose or improve any physiologic or pathologic condition.

Major therapeutic classes include but are not limited to, ACE inhibitors, such as ranitidine, anti-infectives such as antibacterials, antivirals and antimicrobials, vasodilators, including general, coronary, peripheral and cerebral, adrenocortical steroids, alpha-adrenergic agonists, alpha-adrenergic antagonists, selective alpha-two-adrenergic agonists, analgesics, and analgesic combinations, androgens, local and general anesthetics, antiaddictive agents, antiandrogens, antiarrhythmic agents, antiasthmatic agents, anticholinergic agents, anticholinesterase agents, xanthine derivatives, cardiovasculars including calcium channel blockers such as nifedipine, beta agonists such as dobutamine and ritodine, anticoagulants, including heparin, anticonvulsants, antidiabetic agents, antidiarrheal agents, antidiuretic, antiemetic and prokinetic agents, antiepileptic agents, antiestrogens, antihypertensives, such as atenolol, antimigraine agents, antimotionsickness preparations such as scopolamine, ondansetron, meclizine, antinausants, antimuscarinic agents, antiprurtics, antipsychotics, antipyretics, antispasmodics such as gastrointestinal and urinary, antineoplastic agents, antiparasitic agents, anti-Parkinson's agents, antiplatelet agents, antiprogestins, antithyroid agents, antitussives, a typical antidepressants, azaspirodecanediones, barbituates, benzodiazepines, benzothiadiazides, beta blockers, antiarrythmics beta-adrenergic agonists, beta-adrenergic antagonists, selective beta-one-adrenergic antagonists, selective beta-two-adrenergic antagonists, bile salts, medicaments affecting volume and composition of body fluids, butyrophenones, agents affecting calcification, catecholamines and sympathomimetics, cholergic agonists, cholinesterase reactivators, dermatological medicaments, diphenylbutylpiperines, diuretics, ergot alkaloids, estrogens, ganglionic blocking agents, ganglionic stimulating agents, hydantoins, agents for control of gastric acidity, and treatment of peptic ulcers, hematopoitic agents, hisamines, histamine antagonists, 5-hydroxytryptamine antagonists, hyperlipoproteinemia medicaments, hypnotics and sedatives, tranquilizers, hormones, including pituitary hormones such as HGH, HMG, HCG, desmopressin acetate and the like; follicle luteolds, α-ANF, growth factor releasing factor (GFRF), β-MSH, somatostatin, bradykinin, somatotropin, platelet-derived growth factor, asparaginase, bleomycin sulfate, chymopapain, cholecystokinin, chorionic gonadotropin, corticotropin (ACTH), epidermal growth factor, erythropoietin, epoprostenol (platelet aggregation inhibitor), follicle stimulating hormone, glucagons, hirulog, hyaluronidase, insulin like growth factors, m[a]enotropins (urofollitropin (FSH)and LH), oxytocin, streptokinase, tissue plasminogen activator, urokinase, ACTH analogs, ANP, ANP clearance inhibitors, angiotensin II antagonists, antidiuretic hormone agonists, antidiuretic hormone antagonists, bradykinin antagonists, CD4, ceredase, enkephalins, FAB fragments, IgE peptide suppressors, IGF-1, neurotrophic factors, colony stimulating factors, parathyroid hormone agonists, parathyroid hormone antagonists, pentigetide, protein C, protein S, rennin inhibitors, thymosin alpha-1, thrombolytics, TNF, vaccines, alpha-1 antitrypsin (recombinant), and TGF-beta, immunosuppressives, parasympatholytics, parasympathomimetics, psychostimulants, laxatives, methylxanthines, monomine oxidase inhibitors, neuromuscular blocking agents, organic nitrates, opoid analgesics and antagonists, pancreatic enzymes, phenothiazines, progestins, prostaglandins, e.g., alprostadil, agents for treatment of psychiatric disorders, sodium channel blockers, medicaments for spasticity and acute muscle spasms, e.g., muscle relaxants, succinimides, thioxanthines, thrombolytic agents, thyroid agents, tricyclic antidepressants, inhibitors of tubular transport of organic compounds, uterine motility affecting agents, and the like.

Representative medicaments, their analogs and derivatives thereof, included by way of example and not for purposes of limitation, are interferons, e.g., α-2b interferon, amphotericin β, angiopeptin, baclofen, bepridil, buserelin, buspirone, calcitonin, ciclopirox, olamine, copper, cyclosporin, zinc, tropisetron, vapreotide, vasopressin, vasopressin antagonist analogs, verapamil, warfarin, zacopride, zotasetron, cromolyn sodium, diltiazem, felodipine, isradipine, nicardipine, nifedipine, nimodipine, nitredipine, verapamil, isoproterenol, carterolol, labetalol, levobunolol, minoxidil, nadolol, penbuterol, pindolol, propranolol, sotalol, timolol, acebutolol, betaxolol, esmolol, metaproterenol, pirbuterol, ritodrine, terbutaline, alclometasone, aldosterone, amcinonide, beclomethasone, dipropionate, betamethasone, clobetasol, clocortolone, cortisol, cortisone, corticosterone, desonide, desoximetasone, 11-desoxycortiosterone, 11-desoxycortisol, diflorasone, fludrocortisone, flunisolide, fluocinolone, fluocinonide, fluorometholone, flurandrenolide, G-CSF, GM-CSF, M-CSF, GHRF, GHRH, gonadorelin, goserlin, granisetron, halcinonide, hydrocortisone, indomethacin, insulin, insulinotropin, interleukins, e.g., interleukin-2, isosorbide dinitrate, leuprolide, lisinopril, LHRH, LHRH analogs such as buserlin and leuprolide, octreotide, endorphin, TRH, NT-36(- [[(s)-4-oxo-2-azetidinyl]carbonyl]-L-histidyl-L-prolinamide), liprecin, LMW heparin, i.e., enoxaparin, melatonin, medrysone, 6α-methylprednisolone, mometasone, paramethasone, prednisolone, prednisone, tetrahydrocortisol, trimcinolone, benoxinate, benzocaine, bupivacaine, chloroprocaine, dibucaine, dyclonine, etidocaine, mepivacaine, pramoxine, procaine, proparacaine, tetracaine, chloroform, cloned, cyploroane, desflurane, diethyl ether, droperidol, enflurane, etomidate, halothane, isoflurane, ketamine, hydrochloride, meperidine, methohexital, methoxylflurane, nitrogylcerine, propofol, scvoflurane, thiamyal, thiopental, acctaminophen, allopurinol, apazone, aspirin, auranofin, aurothioglucose, colchiine, diclofenac, diflunisal, etodolac, fenoprofen, flurbiprofen, gold sodium thiomalate, ibuprofen, indomethacin, ketoprofen, meclofenamate, mefenanic acid, meselamine, methyl salicylate, nabumetone, naproxen, oxyphenbutazone, phenacetin, phenylbutazone, piroxicam, salicylamide, salicylate, salicylic acid, salsalate, sulfasalazine, sulindae, tometin, acetophenazine, chlorpromazine, fluphenazine, mesoridazine, perphenazine, thioridazine, triflurperazine, triflupromazine, disopyramide, encainide, flecinide, indecainide, mexiletine, moricizine, phenytoin, procainamide, propafenone, quinidine, tocaine, cisapride, domperdone, dronabinol, haloperidol, metoclopramide, nabilone, nicotine, prochlorperazine, promethazine, thiethylperazine, trimethobenzamide, buprenorphine, butorphanol, codeine, dezocine, diphenoxylate, drocode, doxazosin, hydrocodone, hydromorphone, levallorphan, levorphanol, lopermide, meptazinol, methadone, nalbuphine, nalmefene, naloxone, naltrexone, oxybutynin, oxycodone, oxymorphone, pentazocine, propoxyphene, isosobide, dinitrate, nitroglycerin, theophylline, phenylephrine, ephedrine, pilocarpine, furosemide, tetracycline, chlorpheniramine, ketorolac, bromocriptine, guanabenz, prazisin, doxazosin, and flufenamic acid.

Also, representative of medicaments, their analogs and derivatives thereof, which may be delivered are benzodiazepines such as alprazolam, brotizolam, chlordiazepoxide, clobazam, clonazepam, clorazepate, demoxepam, diazepam, flumazenil, flurazepam, halazepam, lorazepam, midazolam, nitrazepam, nordazepam, oxazepam, prazepam, quazepam, temazepam, triazolam and the like; antimuscarinic medicaments such as anistropine, atropine, clininium, cyclopentolate, dicyclomine, flavoxate, glycopyrrolate, hexocyclium, homatropine, ipratropium, isopropamide, mepenzolate, methantheline, oxyphencyclimine, pirenzepine, propantheline, scopolamine, telenzepine, tridihexethyl, tropicamide, and the like; an estrogen such as chlorotrianisene, siethylstilbestrol, methyl estradiol, estrone, estrone sodium sulfate, estropipate, mestranol, quinestrol, sodium equilin sulfate, 17β-estradiol (or estradiol), semi-synthetic estrogen derivatives such as esters of natural estrogen, such as estradiol-17β-enanthate, estradiol-17β-valerate, estradiol-3-benzoate, estradiol-17β-undecenoate, estradiol 16,17-hemisuccinate or estradiol-17β-cypionate, and the 17-alkylated estrogens, such as ethinyl estradiol, ethinyl estradiol-3-isopropylsulphonate, and the like; an androgen such as danazol, fluoxymestetone, methandrostenolone, methyltestosterone, nadrolone decanoate, nandrolone, phenpropionate, oxandrolone, oxymetholone, stanozolol, testolactone, testosterone, testosterone cypionate, testosterone enanthate, testosterone propionate, and the like; or a progestin such as ethynodiol diacetate, gestodene, hydroxyprogesterone caproate, levonnorgestrel, medroxyprogesterone acetate, megestrol acetate, norethindrone, norethindrone acetate, norethynodrel, norgestrel, progesterone and the like.

For example, by employing the device and the applicator hereof, it is possible to electrokinetically deliver medicaments such as anti-virals, for treating human papilloma virus, (HPV), e.g., warts (common, flat, plantar and genital), examples of which are Imiquimod® sold as Aldara™ by 3M for genital warts, a type (HPV), Acyclovir®, sodium salicylate, tretinion, benzoyl peroxide, bleomycin, interferons, Podocon-25, OTC products such as Wart Off by Pfizer and Compound W by MedTech or anti-picornavirus class substances, e.g., Pleconaril, to treat coughs and colds, anti-inflammatory medicaments such as dexamethasone and anti-bacterial agents, proteins, as well as steroids and salts thereof, non-steroidal anti-inflammatory drugs (NSAIDs), and salts thereof, hormones, cytokines, viruses, bacteria, DNA, RNA, (and fragments of both), antihistamines, oligonuceotides, anti-proliferative agents (cancer), specifically 5-fluorouracil (5-FU) and cisplatin, Efudex, or a combination of 5-FU and soviudine, anti-angiogenics such as thalidomide, antibiotics, peptides and peptidomimetics and assemblages of amino acids, phenols and polyphenols, an example of which is PolyphenonE and cosmetic agents, such as retinoids, e.g., hyaluronic acid, vitamins and/or water, skin bulking agents, e.g., collagen, reactive monomers which may polymerize under the skin in non aqueous carriers and be activated by water, botulinum toxins, e.g.

botox, bleaching agents, e.g., Eldopaque 4% by ICN Pharmaceuticals, or a combination of Ketorolac, hydroquinone 4%, Glycolic Acid, lactic acid with suitable vehicle and anesthetics, such as lidocaine, xylocaine, prontocaine, prilocaine, fetanyl, remifentanil, sufentanil, alfentanil, novocaine, procaine, morphine HCL and EMLA either in stand alone fashion or with a vasodilator such as epinephrine. Also, medicaments which inhibit fusion between the plasma membrane and viruses and other adventitious agents to prevent entry by viruses and/or other adventitious agents into cells may also be electrokinetically delivered, e.g., behenyl alcohols such as n-docosanol, its analogs or derivatives. Hair growth may be stimulated by Propecia (finasteride), minoxidil, blocking antidihydrotestosterones or antidihydroestrogens. Hair removal may be accomplished by dyeing the hair and or hair root to facilitate removal by laser means or by electrokinetically using, e.g., dihydrotestostersone or dihydroandrogens or dihydroestrogens. Using pigments, tattoos, either temporary (reversible) or permanent may be applied to a treatment site and tattoos when permanent may be removed using suitable medicaments and the instant invention. Water soluble dyes and decals or templates may be employed in conjunction with the device and applicators. Prostate conditions e.g., prostatitis may be treated with antineoplastics. Additionally, the diagnostic sweat test for cystic fibrosis using pilocarpine, peripheral vascular disease using vasodilators, eye (corneal) treatment using florescein, acne treatments with one or more steroids, NSAIDs, such as ketorolac or medicaments such as Benzamycin, benzoyl perixode, cleocin, T-Stat, over the counter (OTC) products two examples of which are Clearasil and Benzac or Accutane, tazarotene sold as Tazorac, adapalene sold as Differin by Allergan and Galderma respectfully or azelaic acid, a topical cream also sold by Allergan, erythromycin as well as combinations of such medicaments may be electrokinetically delivered. Psoriasis may be treated with an antimetabolite, retinoids, synthetic vitamin D, i.e., calciprotriene, cyclosporin A (CSA), Aristocort, from Lederle, anthrax-derm, by Dermik, methotraxate, cortisone like compounds psoralen or anthalin. Eczema and contact or atopic dermatitis may be treated with corticosteroids or antihistamines. Spider veins may be treated with antiangiogenics, or coagulants (clotting factors or fragmented cellulose polymer). Fluoride treatment of exposed single site hypersensitive dentin may be performed with this device and applicator system. Canker sores and RAS may be treated with, e.g., benzoin or sodium fluoride. Post herpetic neuralgia may be treated with local anesthetics mentioned throughout this disclosure and/or with antivirals, e.g., Acyclovir or combinations of anesthetic and antiviral. Erectile dysfunction may also be treated (transcutaneously at site of concern) using prostaglandins such as PGE or alprostadil, nitroglycerin, and the like or papaverine, yohimbine and the like or sildenafil citrate, i.e., viagra, or apomorphine HCI. Other diagnostic uses i.e., removal or extraction of animal or human bodily material, e.g., fluids, versus delivery of medicament include as examples, allergy screening, e.g., using an electrode mounted array of antigens with a multiplexed-multi-channel application electrode, glucose monitoring and drug testing using electrode mounted specific binders (binder assay) combined with reverse iontophoretic plasma extraction. As a further diagnostic application, body material such as fluids can be extracted into a pad on the electrokinetic device, for example, by reverse iontophoresis. Wounds such as scrapes, cuts, burns, plant allergies, punctures and insect bites or stings can be treated with antihistamines, antibiotics, anti-infectives such as bactracin, Diprolene, topical steroids, and the like, aloe or aloe containing products or OTC products such as Ambesol, Lanocaine and the like, other wound healing agents, such as epidermoid derived growth factors as well as peptides that modulate the inflammatory response and modulators of collagen deposition and modeling as well as other wound healing agents all electrokinetically delivered. Pre-treatment may also include desensitizing agents such as the aforementioned analgesics or salicylic acid. Pruritis, dry skin and keratosis may also be treated using, cortisones and the like, Benadryl itch créme, Lazer créme or EMLA and the like. Actinic keratoses may be treated by electrokinetic delivery of aminolevulinic acid as well as other established antimetabolite agents such as methotraxate, 3% DICLOFENAC IN 2.5% hyaluronic acid, 5FU, 5FU and isotretinion, and the like. Bursitis or mild arthritis may be treated with magnesium sulfate or Dororac from Genderm.

A particular use of the device and applicator hereof is the delivery of Acyclovir® and derivatives and analogs thereof for treatment of recurrent herpetic symptoms, including lesions (oral or genital) and varicella zoster i.e., shingles. Other anti-herpetic medicaments capable of electrokinetic delivery in accordance with the present invention are 5-iodo-2 deoxyuridine (IUDR), cytosine arabinoside (Ara-C), adenine arabinoside (Ara-A), also known as vidarabine, adenine arabinoside monophosphate (Ara-AMP), arabinofuranosyl hypoxanthine (Ara-Hx), phosphonoacetic acid (PAA), thymine arabinoside (Ara-T), 5'-amino-2', 5'-dideoxy-5-iodouridine (AIU), 1-beta-D-arabinofuranosyl-E-5-(2-bromovinyl) uracil (BV-ara-U), also known as sorivudine, 1-beta-D-arabinofuranosyl-E-5 (2-chlorovinyl)uracil (CV-ara-U), two halogenated deoxytidines (BrCdR and ICdR), bromovinyldeoxyuridine (BVDU), trifluorothymidin and Penciclovir®, its prodrug, Famciclovir® and analogs and derivatives thereof, e.g., penciclovir. Most if not all topical agents including both Acyclovir® and IUDR have demonstrated only limited efficacy when applied topically to herpetic lesions, or pre-lesion stage sites including prodomal stage skin sites. However, demonstrably improved clinical results have been achieved when applied electrokinetically, e.g., electrophoretically, to treatment sites. Combinations may also be used including but not limited to IUDR and DMSO. By a treatment site is meant a target tissue, e.g., a diseased tissue or diagnostic site for extraction of a substance, underlying or exposed through or on a human individual or lower animal's skin or mucocutaneous membrane including, the eye and also including, but not limited to body cavity and canal sites such as mouth, ear, nose, vagina, and rectum. Some embodiments would not be appropriate for human infants and lower animals and human application to the animal would obviously replace self-application.

In a first aspect of the present invention, an individual may privately self-administer the medicament by employing the self-powered hand-held device to electrokinetically drive the medicament from an applicator into the treatment site, e.g., through the skin or mucocutaneous membrane to a diseased tissue. Preferably, a low-cost throwaway single-use applicator is used to facilitate the flow of medicament into the skin under the influence of the electromotive force supplied to the medicament contained in the applicator by the self-powered hand-held wireless device. The hand-held device is preferably lightweight, compact, inexpensive and portable and comprises a housing configured for self-manipulation and containing a power source, for example, a battery, connected through first and second terminals and suitable electronics, including a current driver and voltage multiplier, with active and ground electrodes. The active electrode is preferably mounted on the end of the device to facilitate manipulation of the device so that the active electrode may engage the applicator against the skin or mucocutaneous membrane. The second terminal of the power source is connected with the ground electrode, i.e., a tactile electrode, on the surface of the device for electrical contact with a second skin site, i.e., a portion of the individual's hand engaging and manipulating the device. By self-manipulation is meant that the individual can engage the device in one hand or a portion thereof and freely orient the device to engage the active electrode of the device through the applicator or directly through medicament against the skin or mucocutaneous membrane generally wherever the treatment site is located and irrespective of whether an applicator is used and, if used, irrespective of whether the applicator is attached to the device or to the individual's skin or mucocutaneous membrane or interposed therebetween with the device subsequently applied to the applicator.

It will be appreciated that the metal portions of any electrode construction may be of any of a variety of metals or metallic films, foils, screens, deposits, mesh, paints including but not limited to aluminum, carbon, gold, platinum, silver, silver chloride, copper or steel, specifically surgical or similar fine grade steel, titanium, zinc or alloys of the aforementioned materials. These metal materials may also be used as a component of an electrode with a plastic base, form or foundation such as Mylar and the like. It is also possible that if the active and ground electrodes are of dissimilar metals or have different half cell reactions the device may generate part or all of its electrical power by this galvanic couple system of which numerous systems are well known in the art and require no further description. At times when hydration, ancillary or otherwise may be required, surfactants to facilitate the rate of hydration, i.e., wetting action, may be employed in, on or about the medicament applicator electrode with materials such as the surfactant Tween 20 or 85, made by ICI America, Neodol 91-6, from Shell Chemical Co., Terigol 15-S-7 from Union Carbide, Pluronic Poloxamer F68 or F127 from BASF or Duponol C or XL made by Dupont Chemical Corp or isopropyl myristate.

In a preferred embodiment employing an applicator, the applicator preferably comprises a substrate having a reservoir, e.g., an open-cellular structure, for containing a medicament. This preferred open cellular or porous portion forms a minimum barrier to movement of medicament molecules under the influence of the applied current to transport the medicament molecules into the skin or mucocutaneous membrane. The applicator thus forms an electrode for application to the treatment site, e.g., an individual's skin and is preferably applied to the device prior to application of the device and attached applicator to the site. It will be appreciated, however, that the applicator electrode can be applied directly to or adjacent to the treatment site, e.g., by using an adhesive, prior to applying the device to the applicator. To secure the applicator electrode to the device prior to application to the treatment site, an adhesive is preferably employed, although other types of securement may be used, such as complementary hook-and-loop fasteners, tabs, post and hole, magnets or the like. It will also be appreciated that an electrical circuit is completed through the active electrode of the device, the applicator electrode and the treatment site for return through the individual's skin in electrical contact with the ground electrode of the device upon application of the device and applicator electrode to the treatment site. Thus, by grasping the device with the individual's hand or finger in contact with the tactile electrode, an electrical circuit is completed from the device through the applicator electrode, the treatment site, the individual's torso, arm and hand and the tactile electrode. To facilitate completion of the electrical circuit, the applicator electrode may have a portion, which overlies the tactile electrode to facilitate the flow of electrical current. For example, the applicator portion overlying the tactile electrode may be open cellular or porous and may contain an electrically conductive material, e.g., hydrogel. When this applicator substrate portion is pressed against the tactile electrode, electrical contact between the tactile electrode and the individual's skin is facilitated. Auxiliary hydration, e.g., wetting the fingers, the material or the tactile electrode may be employed to further facilitate closure of the current loop in any or all applicator or device embodiments. The hydrogel may also have adhesive properties or may contain an adhesive and thereby serve or additionally serve as a mechanism for releasably securing the applicator to the device.

The medicament may be applied to the applicator by the user just prior to use. Alternatively, the medicament can be prepackaged as a unit dose in the applicator electrode. The medicament also may take many forms, for example, the medicament may be formulated as a liquid, a gel, an ointment, a dry powder, a lotion, a foam, a solution or a cream. Depending upon the nature of the medicament, it may also be electrically conductive per se, or require ancillary substances to transport the medicament, e.g., an electrically conductive substance such as water or very weak trace saline to provide the necessary electrical conductivity. The applicator preferably includes a porous or open multicellular pad to which medicament can be supplied by the user just prior to use or in which the medicament may be prepackaged. Where the medicament is not sufficiently electrically conductive per se, or is not part of a hydrophilic formulation, the user may hydrate the pad of the applicator to render the medicament transportable by the electromotive force of the electrical current flowing through the pad. Preferably, the applicator is releasably secured, e.g., by adhesive, to the device. Alternatively, the applicator can be applied directly to the skin or mucocutaneous membrane on or surrounding the treatment site, for example, by employing a releasable adhesive or the inherent tack of the substance included with the applicator electrode. In either mode of use, when the device, applicator pad and treatment site lie in series contact with one another and the circuit is completed through the individual's skin, electrical current flows through the pad and skin, driving the medicament into the treatment site, e.g., transdermally into an underlying site.

In another form of the invention and as noted above, the medicament can be prepackaged in the pad of the applicator. For example, one or more rupturable capsules containing the medicament can be located in or adjacent to the porous pad, the encapsulation of the medicament affording long shelf life. Alternatively, the medicament may be prepackaged in or adjacent to the cells of a porous pad with removable seals for preventing exposure of the medicament to ambient conditions thereby also affording long shelf life. Further, different applicators can be prepackaged with different medicaments as required for various treatments. With a prepackaged encapsulated, (including micro encapsulation) medicament, the capsule or capsules can be ruptured by the application of pressure to the applicator pad, thereby spreading the medicament in and among the interstices of the pad. Where seals are used in conjunction with a medicament contained in a porous applicator pad, the seals are preferably adhesively secured to the pad and removed. If necessary, the pad can then be hydrated by the user. This may be accomplished using a separate small sterile vial of fluid by which drops of solution are applied. The applicator is then applied by the user to the device or to the skin or mucocutaneous membrane overlying the treatment site or simply interposed between the device and the treatment site. In this manner, the device, applicator electrode and skin or membrane are serially connected with one another for electrokinetic self-administration of the medicament into the treatment site. As a third alternative, both the medicament and an electrical conductor such as water can be encapsulated within the pad. By applying pressure, for example, finger pressure, the medicament and hydrating capsules can be ruptured, intermingling the medicament and water within or adjacent to the porous multi-cellular applicator pad, rendering the medicament electrokinetically transportable under the influence of the current flow. A fourth alternative includes pre-hydrating the pad and sealing the pre-hydrated pad from the medicament. When the seals are broken, the hydrating material hydrates the medicament, enabling electrokinetic delivery of the medicament. Alternatively, the medicament may be encapsulated to isolate it from a pre-hydrated pad. A sixth alternative is to encapsulate the hydration material, e.g., water or water containing electrolytes to enhance conductivity and medicament transport. A seventh alternative is to package the medicament with a hydroscopic material which will allow it to pick up water from the air once it has been removed from its protective packaging.

It will be appreciated that the pad containing the electrically conductive medicament or medicament hydrated to afford electrical conductivity through the pad affords a minimum barrier to the movement of the medicament molecules into the treatment site under the electromotive force applied by the completion of the electrical current. Thus, at least a portion of the substrate or pad is preferably thin and highly porous. The pad should be comfortable to the user and if possible be somewhat flexible so as to conform to the treatment site, providing full contact coverage when in place, e.g., fabrics, absorbent gels, cotton or open celled foam. The pad should also have sufficient interstices or open cells, i.e., porosity, to hold quantities of the electrically conductive medicament or the medicament and hydrating material to afford efficacious treatment, e.g., of herpes treatment sites, over a period of time, for example, up to 15 minutes. For most treatments, the period of application is limited, for example, within a range of 1–30 minutes. The hydrating material is preferably water or a very weak trace saline solution lying within a range of 0.001–0.1%. As an additional example of hydrating material, polypropylene glycol, polyethylene glycol or polyvinyl glycol may be used.

Further, the applicator electrode must be void of any short-circuit paths. For example, where the applicator includes a hydrogel on an applicator portion overlying the tactile electrode of the device, the hydrogel must be electrically insulated from the active electrode and the conductive or hydrated medicament in the pad to ensure that the circuit is completed through the individual's skin rather than merely short-circuited through the device and applicator electrode. The distance between the medicament containing electrically conductive portion and the hydrogel serves as an electrical insulator, particularly where the substrate therebetween is non-wicking. Likewise distance between the active and ground electrodes of the device serve the same purpose. Additional physical barriers may be provided, e.g., spaces, openings, valleys and ridges of non-conductive material on either or both the device and the applicator electrode. When both are employed they may be of a complementary nature, e.g., a valley on the device and a ridge on the applicator electrode. A portion of the barrier may also be hydrophilic so as to absorb any of the small amounts of hydration material which may be employed.

In a further preferred embodiment of the present invention, the applicator may contain a magnet for activating and deactivating the power supply in the device. Consequently, when the applicator electrode is applied to the device or to the treatment site and the device is applied to the applicator, the magnet cooperates with the internal electronics of the device to activate the device. Conversely, upon removal of the applicator from the device or the device from the applicator, the magnet in the electrode deactivates the electrical circuit. Other conventional switching means may also be employed, e.g., toggle, twist or push types or the magnet may be separate from the applicator. The applicator may also contain a code carrying system, e.g., bar code or another state of the art system, which when attached to the hand-held device, programs the device to deliver the correct amount of medicament. This allows the hand held device to be used with a range of medicaments without having to reprogram the hand held unit. Also, indicators may be provided on the device to indicate that the device is actuated such that the user can be assured that the medicament is being electromotively driven into the treatment site. Thus, for example, one or more LEDs may be incorporated in the circuit to indicate activation of the circuit. Other indicators or the same indicator in a different mode, e.g., solid vs. flashing may be employed to indicate when the device and applicator electrode are operating satisfactorily to electrokinetically drive the medicament into the treatment site. An additional indicator can be employed to indicate low battery problems. Also, a variable timing device may be incorporated in the electrical circuit. The circuit may be activated for a selected predetermined length of time and automatically deactivated after that time period has lapsed. Alternately, a timer may offer an event signal or series of signals to the user without necessarily reprogramming the time period. For example, if the treatment is interrupted for a brief period of time, the timer may continue timing the treatment provided the interruption is only brief, e.g., a minute or two. If the interruption is prolonged, the timer is automatically reset to provide a period of treatment which is therapeutically effective. Also, a non-ultrasound generated vibration can be added or used in lieu of the LED to indicate working status of the device and that the device lies in a closed current loop via the individual's body surface.

In another form, the applicator may comprise a splint-like strip for releasable securement to an individual's finger with self-contained electronics, a power source and active and ground electrodes formed integrally with the strip. The applicator strip may have a rectilinear, square, circular or shaped pad as the active electrode adjacent the individual's fingertip. The applicator strip preferably includes a split ring for releasably securing the applicator strip to and along an inside surface of an individual's finger. The applicator pad, which may be integral with or form a disposable pad for the applicator strip, is in contact with the active electrode adjacent the individual's fingertip for application to the treatment site. On the opposite side of the strip from the active electrode and in contact with the user's finger is a ground electrode. The batteries within the applicator strip may be air-actuated by removal of a tab overlying battery terminals. After the applicator strip is secured to the user's finger, the user then places the one-time use disposable applicator pad adjacent the user's fingertip and against the treatment site. This completes the circuit through the site and the user's skin. With the applicator pad separate from the applicator strip, the strip may be reusable with other disposable pads. Alternately, the pad may be a built-in part of the strip with or without pre-packaged medicament and/or hydration means, thereby enabling the whole device disposable. The applicator may also be miniaturized to the extent that it may have a thimble-like configuration without a ring and may be frictionally retained on the tip of the individual's finger.

In another aspect of the present invention, the applicator may comprise a completely self-contained disposable unit having its own electronic circuitry and power source. In this aspect, the applicator may be provided (i) without the medicament and electrically conductive material (e.g., water), (ii) with the medicament in a prepackaged form within the applicator requiring only hydration upon use, if the medicament is not per se electrically conductive, or (iii) with both a medicament and hydration material. For example, the applicator in this form may comprise a flexible substrate having a medicament pad on a treatment site side thereof, an optional hydration material layer, overlaid by a first electrode, electronic circuitry including a power source, e.g., a battery, a second electrode and, optionally, a conductive material such as a hydrogel. By applying the medicament-containing pad to the treatment site and holding the applicator on the site by a finger or hand of the individual pressing on the applicator opposite the site, an electrical circuit is completed through the second electrode, the electronics, the medicament applicator electrode and the skin or mucocutaneous membrane between the site and the individual's finger or hand (i.e., along the finger or hand, the individual's arm, torso and site). Consequently, the medicament is electromotively driven by the electrical current into the site. The self-contained disposable unit may be removed from its package by the individual upon contact of the individual's finger with a tacky hydrogel exposed on the unit after the package is opened. This finger contact with slight finger pressure may cause contact between the hydration material and the medicament prior to removal from the package. Also, the finger contact and removal from the package further allows highly intuitive manipulation of the unit to the treatment site and ease of use given the lightweight and compact size of the unit. The unit may also be placed in a position where the finger contact is replaced by the contact of another grounding site such as would be the case if, by example the unit were placed in the mouth between the gum and inside mucosal tissue of the mouth or if the unit were placed inside the arm and contacted the upper rib cage or if the unit were designed and formed in a fashion similar to a contact lens for ocular treatments. It should be appreciated that the orientation of the active and ground electrodes and placement of the medicament could be reversed in these or other like uses.

The battery for the circuit, for example, a zinc oxide battery, may be of the type activated by exposure to oxygen. In that battery, a tab overlies battery terminals which, when the tab is removed, exposes the contacts to oxygen thereby activating the battery. Various other types of miniaturized power sources may be provided, e.g., film sheet stacked batteries. It will also be appreciated that the medicament may be applied to the applicator pad by the user after the applicator is unpackaged and, if not per se conductive, the pad may also be hydrated by the user prior to application to the treatment site. Alternatively, the medicament may be prepackaged within the pad, for example, in one or more rupturable capsules and if not electrically conductive per se, one or more additional capsules containing hydrating fluid, e.g., a conductive fluid, such as water or saline may be prepackaged in the applicator as well. By squeezing the applicator electrode to rupture the capsule or capsules, the encapsulated medicament and, if necessary, the hydrating fluid, intermingle with one another and provide the necessary electrical conductivity through the applicator pad to enable electromotive transport of the medicament through the skin. It will be appreciated that the grounding electrode lies on the opposite side of the applicator from the active electrode and a circuit is therefore completed through the individual's finger or hand holding the applicator over the treatment site and the individual's arm and torso. To ensure electrical contact with the individual's hand or finger and the ground electrode, the top or outer portion of the applicator remote from the medicament pad may contain a conductive hydrogel.

In a further alternative form hereof, the applicator comprises a self-contained disposable unit likewise having its own electronic circuitry and power source. In this form, the active electrode may form a portion of the applicator spaced from an electrically insulated ground electrode also forming part of the applicator. The applicator is configured such that the first or active electrode of the applicator lies in electrical contact with the applicator pad (electrode). The active applicator electrode is applied to the treatment site and the ground electrode on the applicator is placed in electrical contact with the user's skin. An electrical circuit is thereby completed through the applicator, the applicator electrode and the treatment site with the return circuit through the skin, and the ground electrode of the applicator. The spacing between the active electrode and the ground electrode in electrical contact with the treatment site and the skin, respectively, can be quite small, i.e., on the order of one-half inch.

As mentioned previously, the medicament may be formulated as a liquid, gel, ointment, dry powder, lotion, foam, solution or cream. Where a liquid constitutes the medicament, the applicator electrode for use with the device may include an electrically insulative housing, for example, a torus, for containing the liquid. On one side of and secured to the torus is a microporous film overlaid by a removable barrier, e.g., foil or inert material adhered to the insulated housing to prevent transfer of the liquid within the applicator electrode externally. The opposite side of the insulative housing may likewise be confined by a barrier overlying the housing. The insulative housing preferably has tabs for attaching the applicator electrode to the device similarly as previously described. A conductive plate may overlie the foil or the applicator electrode may be applied to the device directly with the active electrode of the device in electrical contact with the barrier. By removal of the adhesively secured barrier layer and application of the applicator electrode to the site, electrokinetic transfer of the medicament can be accomplished.

In a further form, the active and ground electrodes may be spaced one from the other in a self-contained unit and separated by a malleable or tensioned arm. For example, the ground electrode may be adhesively secured to the individual at a location adjacent the medicament delivery device and the active electrode placed in contact with the site. The springbiased or malleably tensioned arm holds the active electrode with an optional gimbal component in electrical contact with the treatment site in a fully flush or full contact manner, avoiding only partial contact and hence avoiding less than effective treatment. This permits hands' free electrokinetic delivery of the medicament to the treatment site.

In a still further form, a self-contained unit having its own electronic circuitry and power source for hands' free application to the treatment site is provided. In this form, a generally U-shaped clip having opposite ends which mount the ground and active electrodes, respectively, as well as the power source and electronic circuitry, may be applied in a gripping or clamping manner to clip the self-contained unit adjacent the treatment site such that the active electrode engages the treatment site for electrokinetic delivery of the medicament.

In a still further form of the present invention, electrokinetic medicament delivery may be applied in an ocular applicator similar to and worn like a contact lens. The mechanism of the electrokinetic delivery may be multi-channel, for example, as described and illustrated in U.S. Pat. No. 5,160,316, now U.S. Pat. No. Re. 36,626, incorporated herein by reference. Thus, a delivery device similar to a contact lens may be employed to therapeutically treat the conjunctiva for acute glaucoma using as an example, Xalatan or even to contour the eye by delivering agents that retain $H_2O$, such as hyaluronidase or hyaluronic acid, which would swell the conjunctiva in specific sites of the eye. Antiviral drugs foscarnet and ganciclovir either alone or in combination may be electrokinetically delivered for treating herpetic eye infections, e.g., cytomegalovirus (CMV) and CMV retinitis. Differential levels of power and agent delivery are possible with the multi-channel delivery. In this manner, the refraction of the light can be modified by changing or altering the shape of the eye/conjunctiva. The medicament delivery device may be worn or applied periodically for various time periods, for example, within a range of 1 to 60 minutes.

In the above aspects of the present invention, the circuitry limits the maximum current available to the applicator electrode to preferably less than about 1 milliampere per two square centimeters of the skin-contacting surface area of the electrode. Depending upon the working electrode's skin-contacting surface configuration, the current level can vary from about 0.1 to about 1.2 milliamps. While higher currents have been used, user discomfort can be experienced. Buffers could be employed to overcome this milliamp range ceiling. It is also another feature hereof that the electrical current can be ramped up and ramped down, respectively, at the beginning and end of the treatment. See, for example, prior U.S. Pat. No. 5,160,316, now U.S. Pat. No. Re. 36,626, the disclosure of which is incorporated herein by reference. Ramping contours of different configurations can be used, for example, linear, non-linear, exponential, pulsed, or otherwise shaped. Also, while direct current is preferred, alternating current can be used.

In all of the foregoing embodiments, facilitators may be employed to minimize or eliminate the barrier to the transfer of the medicament molecules through the skin. For example, acetic acid or dimethylsulfoxide (DMSO), alcohols, such as ethanol and isoproanol, ethyalactate, sulphoxides, fatty acids, such as oleic acid, lauric acid, capric acid and caprylic acid, sodium lauryl sulfate, acyl lactylates (except in their salt form), e.g., caprol lactyic acid and lauroyl lactylic acid, esters, (1-dedecylazacycheptan-2-one) (Azone), pyrrolidones, such as dodecyl pyrrolidone, dimethyl lauramide, linear dialiphatic or aliphathic, sulfoxides, unsubstituted or mono or di-substituted amides and di-substituted amines among others, urea, cis-urocanic acid or polyoles may be used. It may also be useful in electrokinetic transport of some medicaments to use a second facilitator or skin permeation enhancer which may be a monoglyceride or mixture of monoglyerides of fatty acids such as glycerol monolaurate (GML) or glycerol monooleate (GMO), lauramide diethanolamine (LDEA), or esters of fatty acids having from 10 to 20 carbon atoms. By using these substances, the skin can be disrupted, enhancing the exposure of the dermis to electrokinetic forces. Another type of facilitator is a component which may encase a given molecule within a lipid barrier but makes it less polar and thereby facilitates penetration of the skin by the medicament. An example is gylcesol or phospholipids such as phosphaticylcholine.

It will be appreciated from the foregoing that usage of the device and applicator requires minimal instruction. Where the medicament is prepackaged with the applicator, there are no concerns regarding the dosage as a single unit dosage which is therapeutically effective over the period of application is provided. Moreover, the device and applicator do not require any calibration or settings as the supply of current is fixed by the device electronics. Further, there is no second or ground electrode separate from the device whereby the device is easily used without a separate ground electrode. The power source may be limited to providing only single use longevity. Thus, the power supply may be replaced when a device is reused or the device itself may be discarded. Numerous components may be constructed and linked for short life cycle upon use without negating a prior long shelf life. The applicator and even the device per se are readily disposable.

In a preferred embodiment according to the present invention, there is provided an electrokinetic delivery system for personal use in self-administration of a medicament to a treatment site on an individual, comprising a device for releasable securement to an individual's finger and shaped in part to conform to at least a portion of the individual's finger, at least one of an electrically conductive medicament or a medicament with an electrically conductive carrier therefor, a retainer for releasably securing the device to the individual's finger, a self-contained power source carried by the device, a first electrode carried by the device adjacent a distal end portion thereof and adjacent the tip of the individual's finger upon retention of the device on the individual's finger, the first electrode being in electrical contact with the power source, a second electrode carried by the device for electrical contact with a portion of the individual's finger, the second electrode being in electrical contact with the power source whereby, upon application of the first electrode to a treatment site with the at least one medicament interposed between the first electrode and the treatment site and completion of an electrical circuit through the first electrode, the at least one medicament, the treatment site, the individual's body, the second electrode and the power source, the device causes an electrical current to flow for electrokinetically driving the at least one medicament into the treatment site.

In a further preferred embodiment according to the present invention, there is provided a method of treatment by electrokinetic self-administration of a medicament into a treatment site for an individual, comprising providing a device shaped in part to conform to at least a portion of an individual's finger and having a self-contained power source, first and second electrodes, and a substrate in electrical contact with the first electrode and having an exposed contact surface, providing at least one of an electrokinetically transportable medicament or a medicament with an electrically conductive carrier therefor, releasably retaining the device on the individual's finger, with the second electrode in electrical contact with the individual's finger, providing the at least one medicament in contact with the substrate or the treatment site, while the device remains retained on the individual's finger, placing the contact surface of the substrate into contact with the individual's treatment site and causing electrical current to flow through the first electrode, the electrically transportable medicament or the conductive carrier, the treatment site, the individual's body, the second electrode and the power source to electrokinetically drive the medicament into the treatment site.

In a further preferred embodiment according to the present invention, there is provided a delivery device for self-administration of a substance to a treatment site on an individual, comprising a self-contained disposable applicator including a pad for containing the substance, a power supply, a first electrode overlying the pad and electrically connected to the power supply and a second electrode having a tactile surface in electrical contact with the power supply and lying on a side of the applicator remote from the pad, the second electrode having an electrically conductive material overlying the tactile surface, whereby, upon the individual's hand or a portion thereof in contact with the tactile surface of the second electrode holding the applicator pad against the treatment site, an electrical circuit is completed between the first electrode through the treatment site and the second electrode via the tactile surface, the electrically conductive material and the individual's hand and body for electrokinetically driving the substance into the treatment site.

BRIEF DESCRIPTION OF THE DRAWINGS

FIG. 1 is a schematic illustration of an electrokinetic medicament delivery device for use with an applicator in accordance with the present invention;

FIG. 2 is a perspective view of the device with the applicator applied thereto;

FIG. 2A is a view similar to FIG. 2 of a modified form of the device and applicator;

FIG. 3 is a perspective view illustrating the device and applicator in use by an individual and being applied to a lesion on the individual's chin;

FIG. 9 is a perspective view of a splint-like strip forming a self-contained applicator electrode in accordance with a further embodiment of the present invention;

FIG. 9A is a view similar to FIG. 9 illustrating a further form of the strip of FIG. 9;

FIG. 15 is a side elevational view of a further form of the present invention;

FIG. 27 is a schematic representation of a device for electrokinetically treating a fungal infestation of the nail beds of an individual's fingers;

FIG. 28 is a schematic illustration of the electronics and thimble pad applicator of the device of FIG. 27;

DETAILED DESCRIPTION OF THE INVENTION

Figure 4:
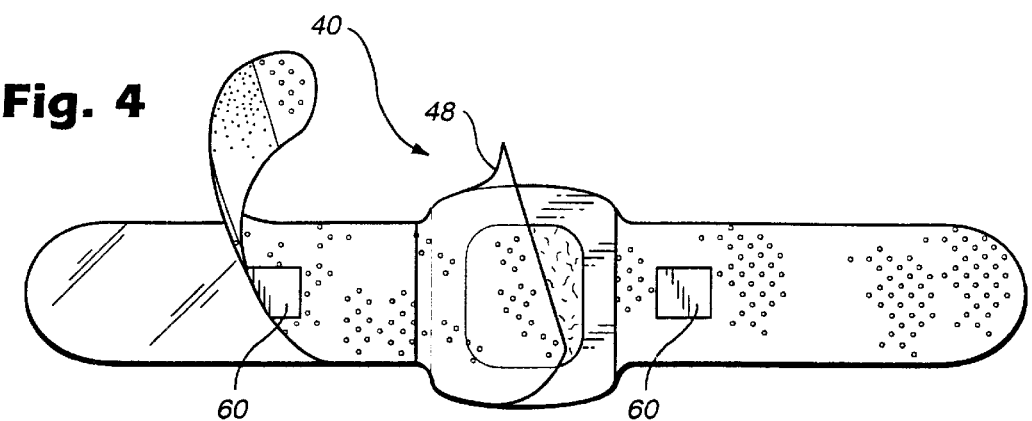
FIG. 4 is a plan view of an applicator from the skin side.

Referring now to the drawing figures, particularly to FIG. 1, there is illustrated a portable, self-contained, lightweight, compact, hand-held electrokinetic medicament delivery device, generally indicated 10, adapted for use with an applicator, described in detail below. The device 10 includes an outer housing 12 containing a power source, for example, a battery 14, and electronic circuitry including a voltage multiplier 16 and a current driver 18. As illustrated, battery 14 includes a first terminal 20 and a second terminal 22. The first terminal 20 is coupled to the voltage multiplier 16 which steps up the voltage supplied by the battery 14 and applies the stepped-up voltage to the current driver 18. Current driver 18 is in contact with a first or active electrode 24 exposed through housing 12, preferably at an end thereof. The second terminal 22 is in contact via a spring 26 and a conductor 28, with a ground or tactile electrode 30 also exposed through housing 12, preferably along a side wall thereof. It will be appreciated that housing 12 is sized and configured to be held within an individual's hand for orientation such that the first or active electrode 24 can be in electrical contact with a treatment site through a conductive medicament-containing pad of an applicator, described below. Thus, in a preferred embodiment, the housing 12 may be of a cylindrical form, with the first or active electrode 24 at one end of the cylinder. It will be appreciated, however, that housing 12 can assume other shapes to facilitate the purposes of device 10, namely to provide a portable, self-contained device having an integral power source which, in conjunction with the applicator, may electrokinetically drive medicament through an individual's skin or mucocutaneous membrane into a treatment site when the applicator and device are applied to and overlie the treatment site. For example, and referring to FIG. 2A, the housing 12a may have a bend intermediate its opposite ends forming a handle 32 at one end having a tactile ground electrode 30a exposed through the handle. The opposite end terminates in an active or first electrode 24a similarly as in FIG. 1. Thus, the handle 32 forms a grip for orienting and manipulating the device 10a relative to the treatment site.

The circuitry limits the maximum current available to the applicator to preferably less than about 1 milliampere per two square centimeters of the treatment site-contacting surface area of the applicator. However, depending upon the working surface of the applicator pad in contact with the site, the current level can vary from about 0.1 to about 1.2 milliamps per two square centimeters to avoid minor discomfort and deleterious side effects. These limitations also apply to each channel of a multi-channel device as discussed herein with reference to U.S. Pat. No. 5,160,316, now U.S. Pat. No. Re. 36,626.

The hand-held device 10 and 10a may be modified to include a piezoelectric element 19 for imparting ultrasonic vibrational motion to the active electrode 24 to further facilitate transdermal or transmucocutaneous delivery of electrokinetically transportable substances, e.g., medicaments. The piezoelectric element 19 is located on the active electrode 24. Power is supplied to energize the piezoelectric element 19 by a conductor 21 connected with the tactile electrode 30, the piezoelectric element 19 being in electrical contact with the active electrode 24. An optional switching element may be used to energize the piezoelectric element or not, as desired, depending upon the particular treatment mode. The combination of an electrokinetically delivered substance into a tissue, together with inducing an ultrasonic vibration in the tissue, enables an opening of pores further facilitating penetration of the medicament. It also facilitates removal of coloration, such as a blemish, freckle or tattoo within the skin by delivery of a suitable bleaching agent, provided as the medicament in the applicator, which will now be described.

Figure 5:
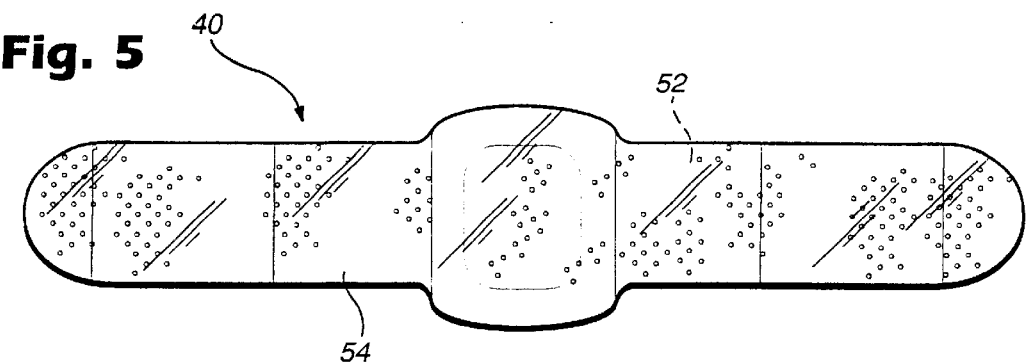
FIG. 5 is a plan view of the applicator from the device side.
Figure 6:
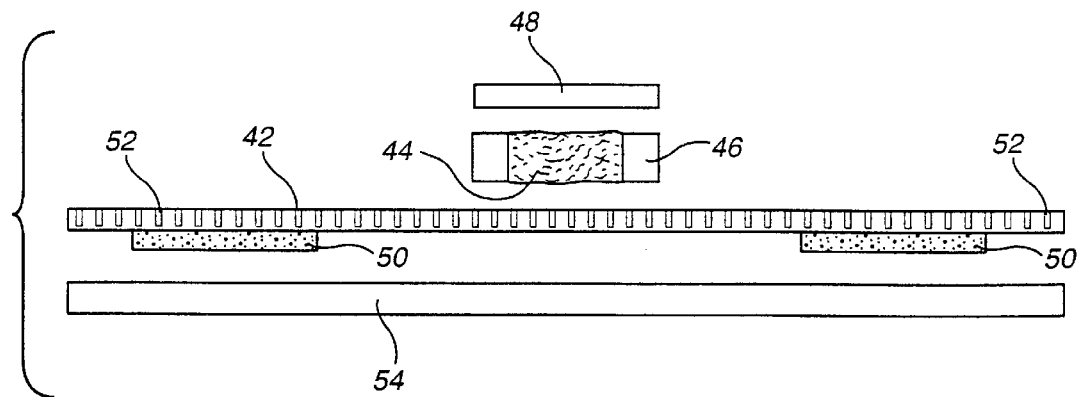
FIG. 6 is an exploded side elevational view illustrating the various parts of the applicator.

Referring to FIGS. 4–6, there is illustrated an applicator, generally designated 40, having a treatment site-contacting side and a device-contacting side as illustrated, respectively, in FIGS. 4 and 5. As best illustrated in FIG. 6, applicator 40 includes a substrate 42 formed of a porous open cellular material. A suitable substrate material may comprise a fabric manufactured by Cerex of Pensacola, Fla., identified as Type DN, Group DN07&DN15. Other suitable types of materials may also be used, provided those materials, at least in the portion of the substrate through which the medicament will be transported to the treatment site, constitute a minimum barrier to the transfer of the medicament molecules from the applicator to the site. On the skin or mucocutaneous side of the applicator 40 as illustrated in FIGS. 4 and 6, there is provided a pad 44 surrounded by a containment barrier 46. The pad may likewise comprise a porous open-cellular material similar to the substrate but preferably comprises a more dense material such as cotton for retaining the medicament. Cotton is sufficiently porous and open-cellular to enable the medicament to be electromotively driven from the cotton pad into the site. It will be appreciated that the pad 44 should be inert to the medicament, as well as non-corrosive and stable when in contact with the medicament. While cotton is preferred, other suitable materials may include plastic pads such as polyethylene, paper, porous ceramics, open-celled porous polytetrafluoroethylene, polyurethane or other plastics, as well as open-celled silicone rubber and vinyl.

The containment barrier 46 is formed of a non-electrically conductive material, which prevents the medicament from weeping or wicking onto portions of the substrate adjacent the medicament pad. Preferably, however, barrier 46 comprises a closed-cell foam, for example, a foam manufactured by Avery Dennison of Pasadena, Calif., identified as Avery Foam Med 5637. While not shown, the foam is preferably adhesively secured to the substrate 42 with margins of the pad 44 frictionally or adhesively retained within the peripheral confines of the barrier 46. A flap 48 overlies the exposed side of the pad and is preferably adhesively secured along one side to one side of the barrier 46 such that the pad 44 can be exposed by lifting or removing the flap. It will also be appreciated that the pad 44 may be incorporated or embedded in the substrate 42. For example, the pad 44 may reside in a cutout portion in the substrate.

On the device side of the applicator and on opposite sides of the pad 44, the substrate extends to form wings 52 for releasably securing the applicator to the device. Preferably, a releasable contact adhesive 50 is applied to the applicator wings 52 for releasably securing the applicator to the device 10. For example, as illustrated in FIG. 2, the applicator 40 illustrated in the form of a strip has a central portion of the strip, i.e., the pad 44, overlying the active electrode 24 at the end of housing 10 with the applicator wings 52 folded along opposite sides of the housing 10 and releasably secured thereto by the adhesive 50. A release liner 54 is provided on the device side of the applicator overlying adhesive 50 and which liner 54 is removed by the user upon application of the applicator to the device. It will be appreciated that other methods of releasably securing the applicator to the device may be employed. For example, hook-and-loop type fasteners may be used with the hooks or loops on the device and the loops or hooks on the applicator. Magnets or spring clips or other mechanical-type fasteners may be employed. The applicator as illustrated in FIGS. 4–6 is also illustrated in the form of a strip similar to a Band-Aid. It will be appreciated, however, that other configurations and shapes of the applicator may be employed, depending upon the configuration of the device. For example, an applicator 40a having a pad formed of similar material as pad 44 may be employed for use with device 10a of FIG. 2A. Applicator 40a may be formed in a circular configuration without wings and may be adhesively or otherwise secured to the active electrode 24a of housing 12a. For example, the peripheral margin of the applicator 40a may have a releasable adhesive for releasable securement to the active electrode 24a on the end of device 10a. In this form, the applicator need not have conductive portions overlying the ground electrode 30a. It will also be appreciated that the applicator is formed of a flexible material generally conformable to the treatment site surfaces to the extent possible given the shape of the active electrode 24, 24a on the device 10, 10a.

The applicator 40 is intended for a single use. That is, once the medicament has been electrokinetically driven from pad 44 into the site, the applicator may be removed from the device or the site and discarded. Where the medicament is prepackaged with the applicator, a coloring agent can be employed, such as iodine, which turns color upon contact with the starch in the open-celled material to visibly indicate that unit dose medicament has been used. Other types of coloring agents can be used to indicate usage of the applicator, e.g., pH indicators, wet saturation indicators or oxidizable pigments.

Figure 7:
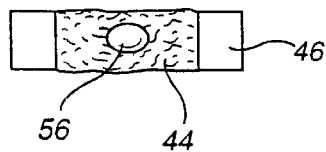
FIGS. 7 and 8 are views of the applicator pad, respectively, illustrating an encapsulated medicament and a combination of encapsulated medicament and hydration fluid within the applicator pad.
Figure 8:
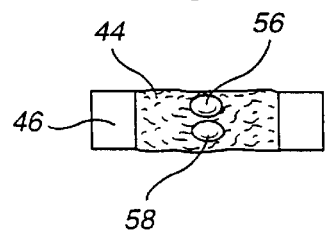

The applicator may be provided to the user without medicament within the applicator pad 44. Thus, when using the applicator, the user may apply the medicament to the applicator pad 44 such that the medicament lies within the interstices of the material of the pad 44. If the applied medicament is not per se conductive, the pad containing the medicament may be hydrated by the application of water, for example, by using an eyedropper. In a preferred form, however, the medicament is supplied and prepackaged with the applicator. For example, the medicament may be contained within a rupturable polymer reservoir or capsule 56, as illustrated in FIG. 7. By encapsulating the medicament, a long shelf-life is assured. To use the applicator with the encapsulated medicament, the capsule 56 can be ruptured by applying pressure to the pad 44, for example, by pressing the pad between the individual's fingers or against the active electrode when the applicator is applied to device 10, or against a surface of packaging in which one or more of the applicators are provided. By rupturing the capsule, the medicament permeates the interstices of the pad 44. If the medicament requires hydration to afford electromotive transport into the treatment site, e.g., a lesion upon application of the electric current, the user may hydrate the pad similarly as previously described. Alternatively, an additional one or more capsules containing hydrating material, e.g., water or saline, may be prepackaged with the applicator. A very weak trace saline solution within a range of 0.001–0.1% and preferably less than 0.05% may be used. As illustrated in FIG. 8, the pad 44 includes one or more medicament capsules 56 and one or more hydration capsules 58. By applying pressure to the two or more capsules, the capsules may be ruptured and the medicament and hydration material intermingled with one another within the interstices of the pad 44, rendering the applicator pad susceptible to conducting current for the electrokinetic delivery of the medicament to the lesion.

Referring back to FIGS. 4–6, a magnet 60 is preferably incorporated into the substrate 42 on one or opposite sides of the pad 44. The electrical circuit in the device may therefore include a magnetic field responsive switch for actuating and deactuating the electrical circuit. Thus, when the applicator is applied to the device, the circuit is activated and when removed, the circuit is deactivated.

Instead of or in addition to the adhesive 50, a conductive gel may be provided within the wings 52 of the porous substrate 42. It will be appreciated that as the applicator electrode is applied to the device 10 (FIG. 2), the wings 52 of the substrate overlie the tactile electrode 30 of the housing 10. The conductive gel thus facilitates electrical conductivity between the individual's fingers or hand overlying the wing portions of the applicator and the tactile electrode 30 to complete the circuit. Thus, the cells of the substrate on one or both wings 52 may be provided with a conductive substance, e.g., a hydrogel. These wings with hydrogel are electrically insulated from the pad 44 and the medicament. Thus, electrical insulating barriers may be provided between the pad 44 and the conductive wing or wings. Such barriers may comprise substantial spacing between the pad and wing with non-conductive material therebetween or physical barriers such as openings, ridges or valleys in the substrate portions interconnecting the pad 44 and the one or more wings of conductive material.

To use the combination device and applicator illustrated in FIGS. 1–8, the applicator 40 is preferably applied to the device by aligning the pad 44 with the active electrode 24 on the end of housing 12. The wings of the applicator are folded along opposite sides of the device and adhered or held to the device overlying the ground electrode 30. With the substrate being at least partially open celled, porous, or cutout, e.g., to contain medicament in gel, solution, cream, foam, ointment or liquid form, the individual's fingers pressing against the substrate and/or the tactile electrode 30 complete an electric circuit path between the device and the individual. Where hydrogel is applied to the wings 52 of the applicator 40, the hydrogel facilitates the completion of the circuit between the individual's hand or finger and the tactile electrode. Whether hydrogel is employed or not the individual may add water to his/her fingers or hand, thus facilitating electrical conductivity. With the applicator 40 applied to the device, the device is actuated, for example, by locating the magnet 60 in a position to close the magnetic switch within the electrical circuit. A conventional on/off switch may be used in lieu of the magnetic switch. The active electrode 24 is also in electrical contact with the medicament containing pad 44 by contact therewith. By manipulating the device, the pad 44 of the applicator is brought into the contact with the treatment site on the individual's skin. Upon contact, electrical current flows between the active electrode 24 in the handpiece, through the medicament-containing pad 44 into the treatment site, through the patient's skin, along the torso and arm for return through the finger or hand to the ground electrode 30. Consequently, the medicament is electromotively transported through the individual's skin or mucocutaneous membrane, thus enhancing local delivery of the medicament to the treatment site.

When using the device 10a of FIG. 2A, the applicator 40a may be secured to the end of housing 12a overlying the active electrode 24a or applied to the treatment site. The individual holding the device 10a makes electrical contact with the ground electrode 30a of the handle 32 by grasping the handle. To ensure good electrical contact, the individual may also add water to his/her fingers or hand. The device 10a is then manipulated to contact the active electrode 24a through the applicator 40a with the treatment site thereby completing the electrical circuit similarly as in the embodiment of FIG. 2.

The device per se may also be applied to a treatment site without a medicament, e.g., without use of the applicator 40 or 40a. The current delivered to the treatment site by the device alone or with or without ultrasonic application or enhancement has beneficial and healing effects in the treatment of the various maladies noted previously.

Figure 10:
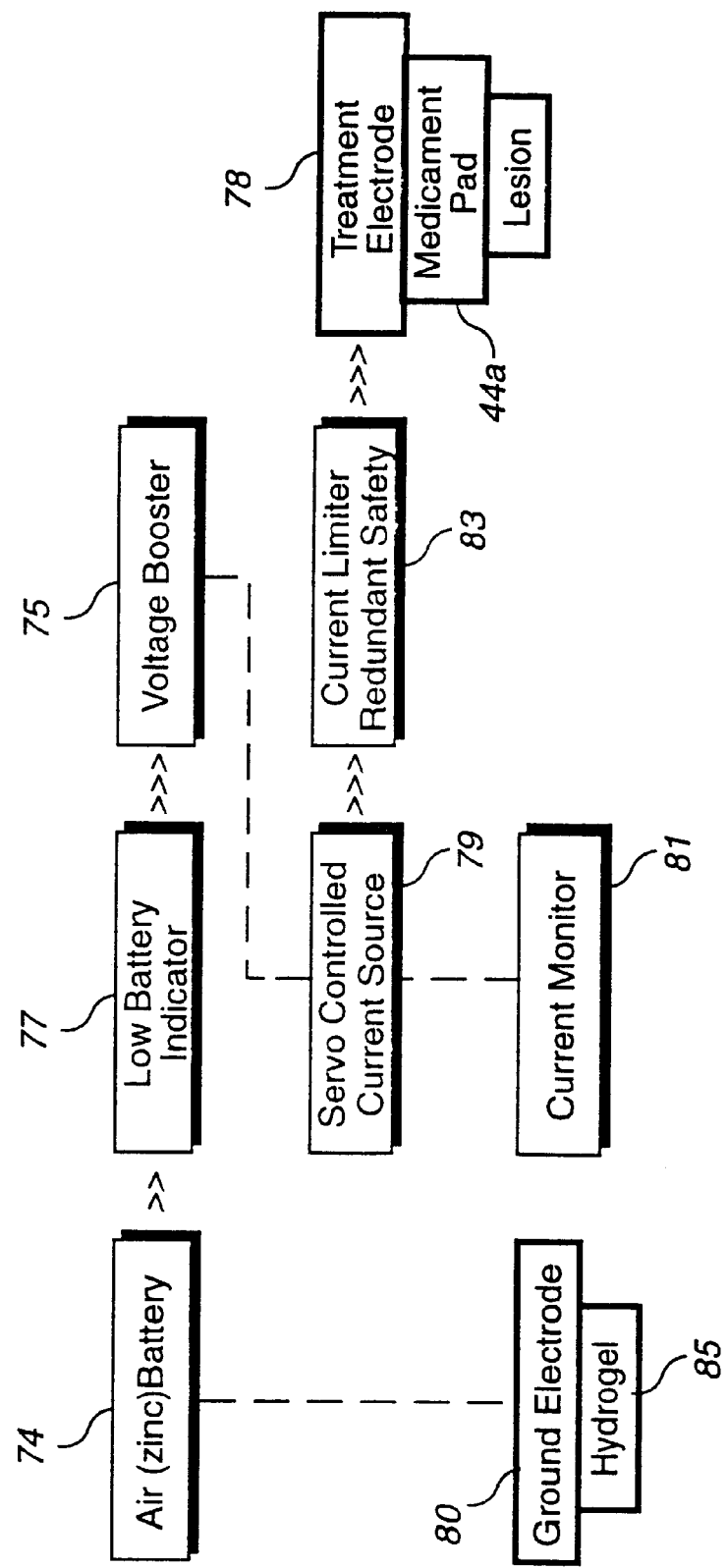
FIG. 10 is a schematic view of an electrical circuit for use with the applicator electrode of FIG. 9.

Referring now to the embodiments hereof illustrated in FIGS. 9 and 10, there is illustrated a completely self-contained disposable unit containing electronic circuitry and a power source for electrokinetically delivering medicament to a treatment site. As illustrated, the self-contained unit, generally designated 70, includes a semi-flexible substrate 72, for example, formed of a plastic material, for underlying an individual's finger and shaped according to the inside surface of an individual's finger. The substrate 72 passes along one or more of the finger joints. The substrate 72 includes batteries 74, for example, conventional zinc oxide batteries which may be actuated by removal of a tab exposing battery contacts to the atmosphere. Additionally, the substrate 72 includes electronics 76 for supplying a flow of current to an active electrode 78 carried at the fingertip end of the substrate 72 and angled relative to the linear extent of substrate 72. It will be appreciated that the active electrode 78 is electrically coupled to the electronics 76 and batteries 74. Additionally, a ground electrode is electrically coupled to the other terminal of batteries 74 and is electrically insulated from the active electrode 78. The ground electrode 80 may comprise a flexible material, portions of which may be in the form of a split ring 82. Thus, the full length of the individual's finger may be in contact with the ground electrode, affording a good electrically conductive contact therewith. Additionally, a retainer, for example, a retaining strap 73, is provided adjacent the inner end of the substrate 72 to, in addition to the split ring 82, releasably secure the applicator electrode to the individual's finger. The retaining strap 73 may include semi-rigid arcuate split ring portions, a full ring integral with substrate 72 or a flexible strap with fasteners to secure the strap ends to one another, for example, hook-and-loop type fasteners.

A similar self-contained unit 70a is illustrated in FIG. 9A wherein like parts are designated by like reference numerals followed by the suffix "a." The substrate 72a extends along the underside of an individual's finger but only along the finger from its tip, past the first joint and terminating short of the second joint. As in the embodiment of FIG. 9, substrate 72a includes batteries 74a, electronics 76a, an active electrode 78a at the fingertip, and a ground electrode 80a including split ring 82a. Additionally, the tip 71 of the substrate 72a may curve back over the fingertip to assist in securing the substrate to the fingertip.

The electronic circuitry for the applicator electrodes 70 and 70a of FIGS. 9 and 9A is illustrated in FIG. 10 and which circuitry is applicable to all embodiments hereof. The power supply for the device 70 includes an air-activated battery 74, coupled through a voltage booster 75 by way of an optional low battery indicator 77. The air-activated batteries may be replaceable and other types of small batteries, such as lithium disks, could be used. The voltage booster 75 is connected to a servo controlled current source 79 and, optionally, to a current monitor 81. The current source 79 is electrically coupled to a current limiter 83 for limiting the current applied to the active electrode within the limits previously discussed. The current limiter 83 is coupled to the treatment electrode 78. In FIG. 10, the treatment electrode is illustrated as applied to the treatment site, e.g., a lesion, through a medicament pad 44a. The ground electrode is also illustrated as applied to the skin by way of an optional electrically conductive hydrogel 85. The medicament pad 44a may be releasably or permanently secured to the device 70, preferably in overlying relation to the active electrode 78. Thus, the device 70 may be a one-time-use disposable or, if the pad is separate, the device 70 may be reused with additional pads. The overlying pad 44a may contain a prepackaged medicament M or any of the alternative combinations of pad, medicaments and hydration disclosed in this application. Alternatively, the pad 44a may be provided in a separate package with the medicament in capsulated form as previously described. In either case, the medicament pad is applied between the active electrode 78 and the treatment site. By removing the tab overlying the battery terminals, the power supply is activated. This may be accomplished when opening the packaging or upon removal of the device from the packaging. When the active electrode 78 is placed in contact overlying the treatment site surface, the circuit is completed through the individual's body, including the finger in contact with the ground electrode.

The applicator 70 is preferably a single-use applicator which may be discarded after use. In an alternate form, the substrate 72 may be shaped in the form of a thimble for overlying the entirety of the fingertip of the individual. The electronics 76 and batteries 74 may be formed on the back side of the thimble opposite the side containing the active electrode, with the ground electrode lying along the inside surface of the thimble and electrically insulated from the active electrode.

Figure 11A:
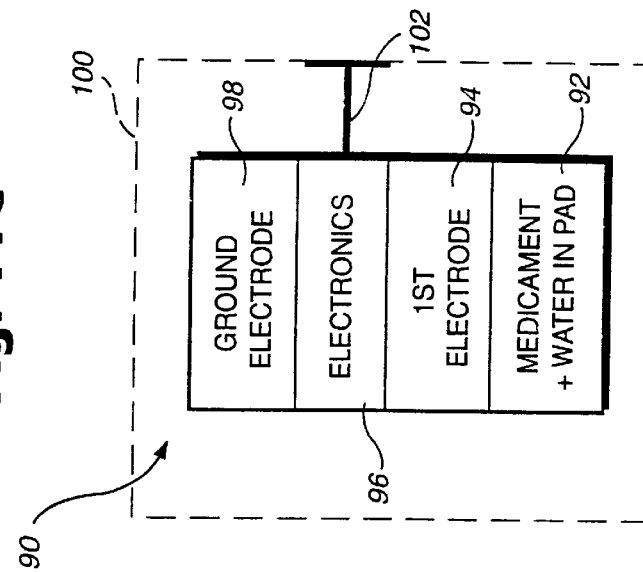
FIGS. 11A, 11B and 11C are schematic representations of a self-contained applicator illustrating the layers of the applicator within a packaging material.
Figure 11B:
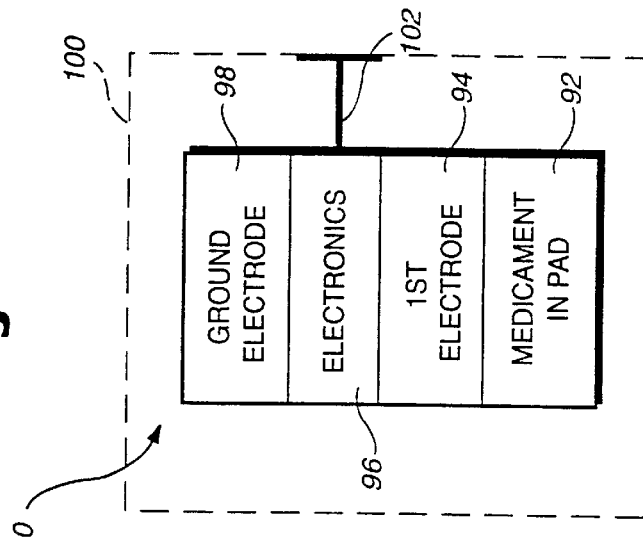
Figure 11C:
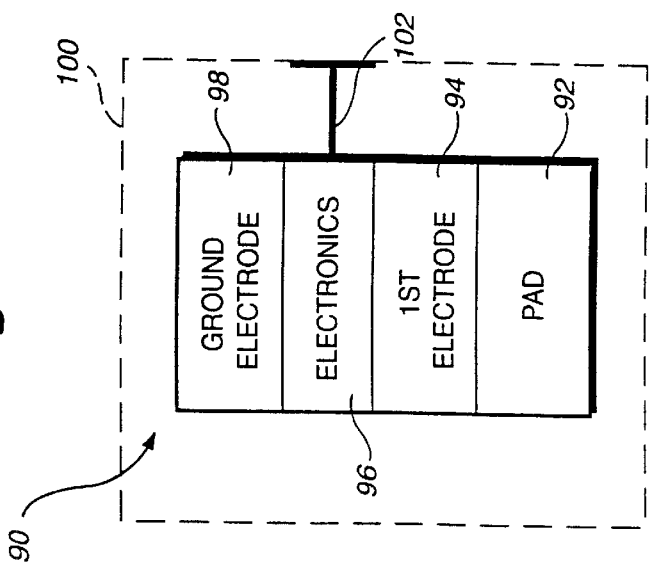

Referring now to FIGS. 11A–11C, there is provided a further form of the applicator hereof comprised of a completely self-contained disposable unit or applicator 90 integrally containing the electronic circuitry and a power source. In this form, the applicator is prepackaged for one-time usage. For example, as illustrated in FIG. 11A, the applicator 90 comprises a pad 92 for containing the medicament and, if necessary, a hydrating fluid. Overlying the pad 92 is the first active electrode 94 electrically connected to electronics 96 within the applicator and which electronics 96 includes a power supply, for example, a battery, and the necessary electronics for flowing a current of a magnitude previously discussed through the pad to electrokinetically drive the medicament into the treatment site. Overlying the electronics is a ground electrode 98, the surface of which remote from pad 92 comprises a tactile surface. Illustrated by the dashed lines is a packaging material 100, for example, plastic packaging typically employed for sterilized packages whereby the applicator 90 may be sealed within the material 100. With the medicament prepackaged within the pad 92, the user opens the package 90. In a preferred form, the applicator 90 is connected with the packaging 100 via a tab 102. By removing the applicator 90 from or opening the packaging material 100, the tab 102 uncovers the battery terminals whereby the power supply is activated. In FIG. 11A, the applicator is provided without the medicament. The user applies the medicament to the pad, hydrates the pad if necessary, and applies the applicator to the treatment site. By applying the pad directly over the treatment site and pressing a finger on the tactile surface of the ground electrode, i.e., on the opposite side of the applicator from the pad, an electrical circuit is completed through the individual's finger and body and through the first electrode, the pad and treatment site whereby the medicament within the pad is electromotively transported to the site. To facilitate good electrical connection, the ground electrode may have an electrical conducting fluid, e.g., hydrogel, overlying its tactile surface.

In FIG. 11B, the medicament is prepackaged in the pad 92. In FIG. 11C, both the medicament and the hydrating fluid is self-contained in the pad. For example, the medicament and the hydrating fluid can be provided in capsules rupturable by pressure applied between the opposite surfaces of the pad before, during or after removal of the applicator from the package 100. Further, a very weak, e.g., less than 0.05% saline solution encapsulated and integrated between the active foil electrode 94 and the medicament with or without a porous matrix reservoir interposed between the encapsulated hydration fluid and the medicament may be employed. Alternatively, adhesively attached or otherwise releasably attached seals for sealing the medicament and the hydration fluid, if necessary, to the applicator to ensure long shelf life and integrity of the foil electrode can be provided.

Additionally, the unit of FIGS. 11A–11C may have a tacky substance, e.g., hydrogel, not shown, overlying the ground electrode 98 within the package 100. Upon opening the package, the individual may contact his/her finger on the tacky substance, facilitating removal of the unit from the package 100. This finger contact on the ground electrode side of the unit also facilitates ready, direct and intuitive manipulation and application of the unit to the treatment site by the individual.

Figure 12:
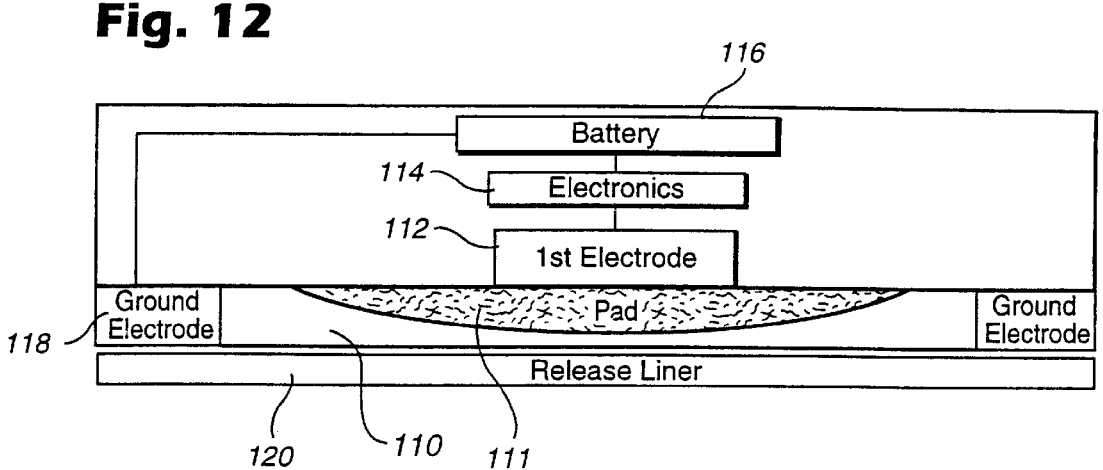
FIG. 12 is a schematic representation of an applicator in accordance with a further embodiment of the present invention.
Figure 13:
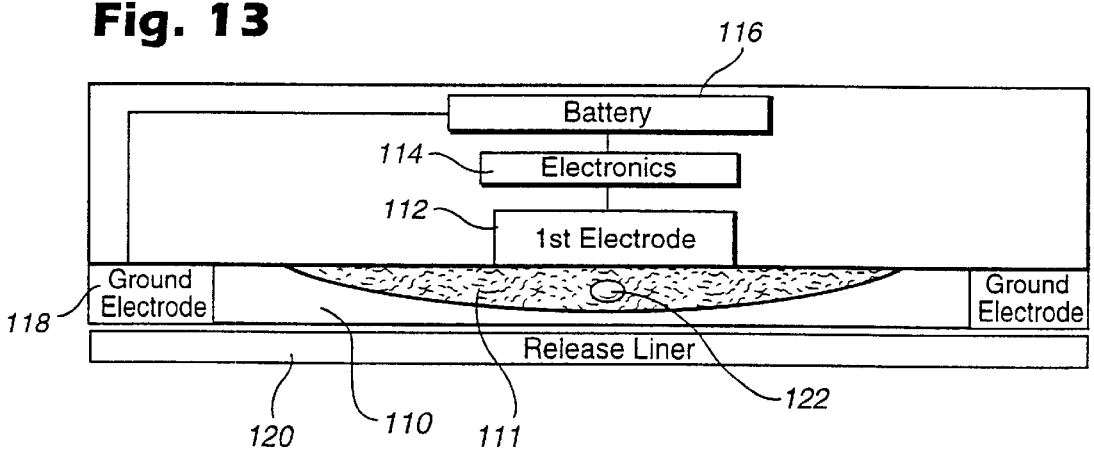
FIGS. 13 and 14 are preferred forms of the applicator of FIG. 12 with an encapsulated medicament illustrated in FIG. 13 and encapsulated medicament and hydrating fluid illustrated in FIG. 14.
Figure 14:
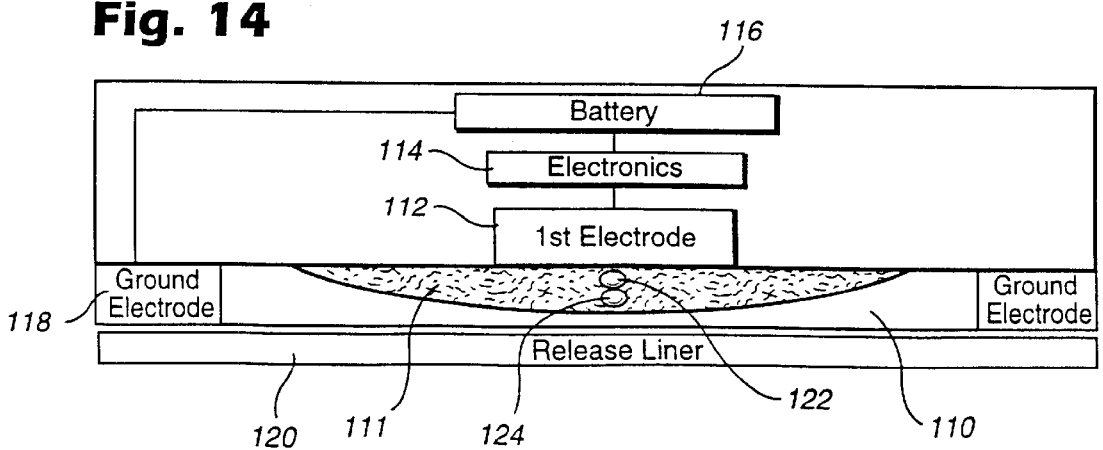

Referring now to the embodiment hereof illustrated in FIGS. 12–14, there is illustrated a further form of applicator body or substrate 110 which comprises a self-contained disposable unit having integral miniaturized electronic circuitry and a power source. In this form, the applicator may comprise a rectilinear or circular article having a centrally located pad 111 and electronic circuitry superposed over the pad. Thus, a first or active electrode 112 overlies the pad and the electronics previously described may overlie the first electrode. The battery 116 may overlie the electronics. The first terminal of the battery is connected through the electronics with the first electrode which, in turn, is in electrical contact with the pad 111. The second terminal of the battery is in contact with a ground electrode 118. The ground electrode may be provided around the margin of the applicator surrounding the pad. For example, if the applicator is shaped in the form of a circle, the ground electrode may comprise an annulus surrounding and electrically insulated from the pad 111. Alternatively, if the applicator is rectilinear, the ground electrode may comprise the margin of the rectilinear applicator or lie at one end of the applicator. In this form, the electrical circuit is completed between the ground electrode and the pad. The distance between the ground electrode and the pad may be on the order of one-half inch or more. The ground electrode need not surround the pad but may be located to one side of the pad a suitable distance from the pad for completing the return circuit path through the skin between the treatment site and the ground electrode.

In the applicator illustrated in FIG. 12, the pad may be provided without the medicament and the user may apply the medicament to the pad upon removal of release liner 120. The battery may be of the air-actuated type previously discussed. Thus, the user, upon applying the medicament to the pad and removing the tab from the battery, may apply the applicator over the lesion, holding both the ground electrode about or spaced from the treatment site and the pad in contact with the treatment site. This completes the electrical circuit through the applicator and the individual's skin between the ground contacting surface and pad contacting surface. If desired, adhesive may be provided on the underside of the applicator body 110 and overlaid by the release liner 120 to releasably adhere the applicator including the pad 111 and ground electrode 118 to the individual's skin and overlying the treatment site. Upon completion of the treatment, the applicator may be discarded.

Alternatively, as illustrated in FIG. 13, the applicator may be prepackaged with the medicament encapsulated within the pad. The capsule is indicated at 122. If the medicament is itself electrically conductive, the individual may apply pressure to the pad to rupture the capsule, spreading the medicament into the interstices of the pad. This can be accomplished while the applicator remains in its packaging. By applying the applicator to the treatment site similarly as previously described in connection with FIG. 12, the circuit is completed whereby the medicament is electrokinetically driven into the site.

In FIG. 14, both the medicament and a hydrating fluid are encapsulated in the pad. The medicament and hydration fluid capsules are indicated at 122 and 124, respectively. The applicator of FIG. 14 is employed similarly as described with respect to FIGS. 12 and 13 after the user ruptures the capsules to intermingle the electrically conductive water and the medicament.

Referring now to FIG. 15, there is illustrated a device 130 similar to the device of FIG. 1 and containing a power source, electronic circuitry including a voltage multiplier and a current driver and a tactile electrode 132 exposed through an outer surface of the device 130. Instead of having the active or first electrode fixed to the end of the device 130, the active electrode 134 is mounted on the device 130 for movement in an axial direction. The movement is designed to open or close a pressure actuated switch in the electronic circuitry to activate the device. Thus, the active electrode 134 in an outermost position maintains the electronic circuitry in an off condition. Pressure applied to the first or active electrode 134 tending to displace it toward the device housing closes the switch, activating the electronic circuitry for electrokinetic delivery of the medicament.

In this form of the invention and instead of an applicator releasably secured to an electrokinetic device, the distal face of the first electrode 134 may be provided with an electrical insulator ring 136 defining and surrounding a reservoir 138. It will be appreciated that the medicament can be supplied from an ancillary tube, jar or the like in the form of a gel, cream, foam or the like and disposed by the user into the reservoir 138 within the insulating ring 136 prior to use. With the reservoir filled with medicament, the device can be applied to the treatment site similarly as the device of FIG. 2 is applied to the treatment site. By applying a slight pressure on the device toward the treatment site, the electrical circuit is closed. Thus, the medicament within the reservoir is electrokinetically motivated into the treatment site, the electrical circuit being completed through the treatment site, with the medicament, the first electrode 134, the electronics, the tactile electrode 132 and the individual's hand and skin between the tactile electrode and the treatment site.

Figure 16:
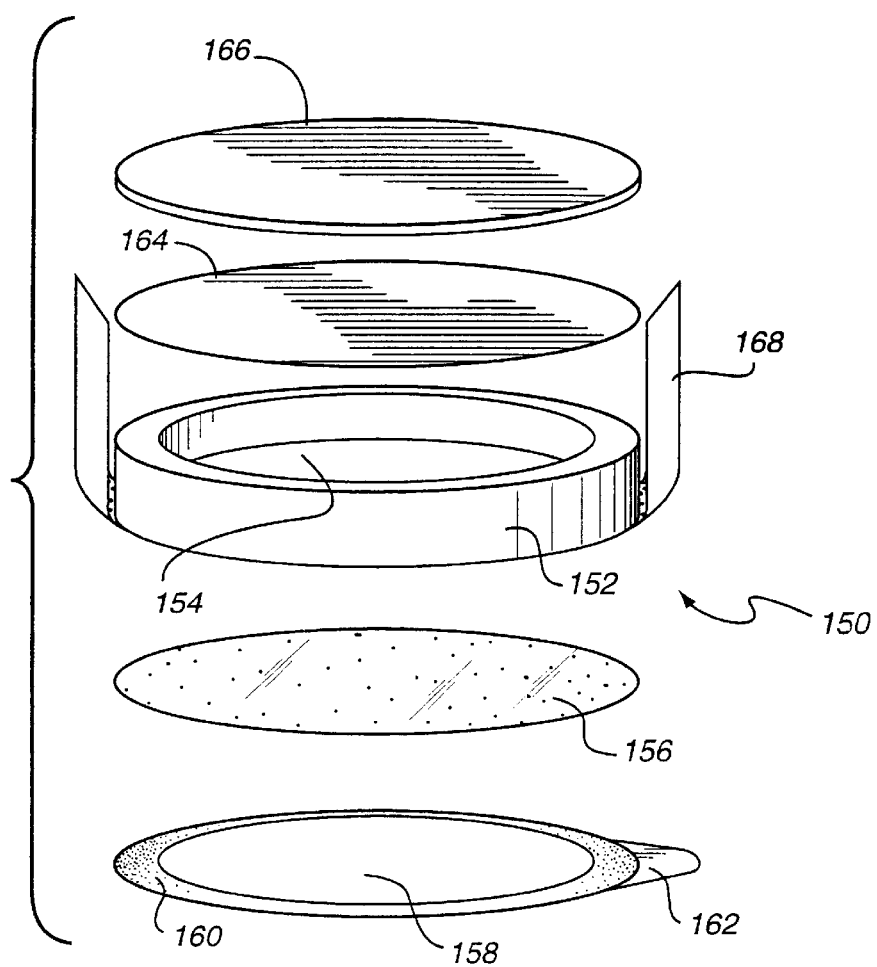
FIG. 16 is an exploded schematic view of a still further form of applicator electrode in accordance with the present invention.
Figure 17:
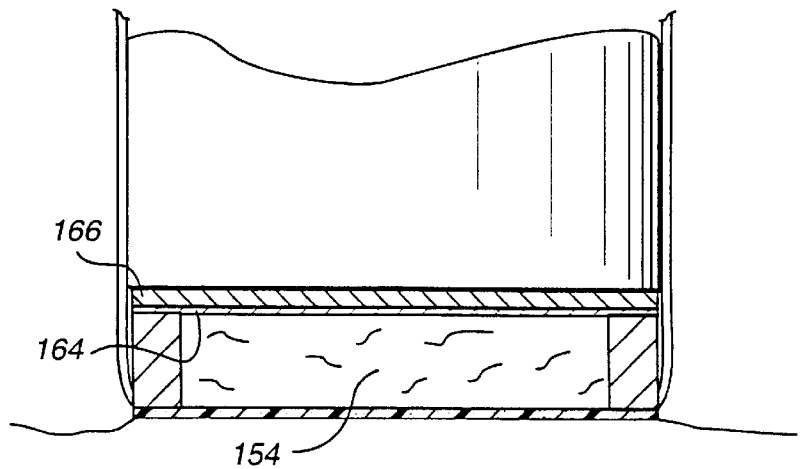
FIG. 17 is a fragmentary view of the applicator of FIG. 16 applied to the end of a device.

Referring now to FIGS. 16 and 17, there is illustrated a further form of applicator in accordance with the present invention. In this form, an applicator, generally designated 150, may be used in conjunction with the device illustrated in FIG. 1 and which applicator is particularly useful for electrokinetically delivering a liquid medicament. The applicator 150 may comprise an insulated annular housing 152 in the form of a torus having a central reservoir 154 for confining the liquid. One side of the housing 152 comprises a microporous film 156 overlaid by a barrier, e.g., foil or inert tab 158. The margin of the tab 158 has releasable adhesive 160 such that the barrier can be releasably attached to one side of the housing 152. The barrier tab includes a finger tab 162 for ready removal of the barrier 158 from the applicator. The opposite end of the reservoir 154 is closed by a similar barrier layer 164 or by an optional conductive plate 166. Additionally, tabs 168 are secured along opposite sides of the housing 152 for releasably securing the housing 152 to the device, e.g., illustrated in FIG. 1.

As illustrated in FIG. 17, the active electrode of the device bears against the optional conductive plate 166 which conducts electricity through the barrier layer 164 into the liquid medicament in the reservoir 154. Upon removal of the tab 158, the liquid medicament when applied to the treatment site can be electrokinetically driven into the treatment site through the microporous film 156. As noted previously, the liquid within the reservoir may be per se conductive or, if not conductive, may be provided with a carrier whereby the medicament can be driven through the porous membrane 156 into the treatment site.

Figure 18:
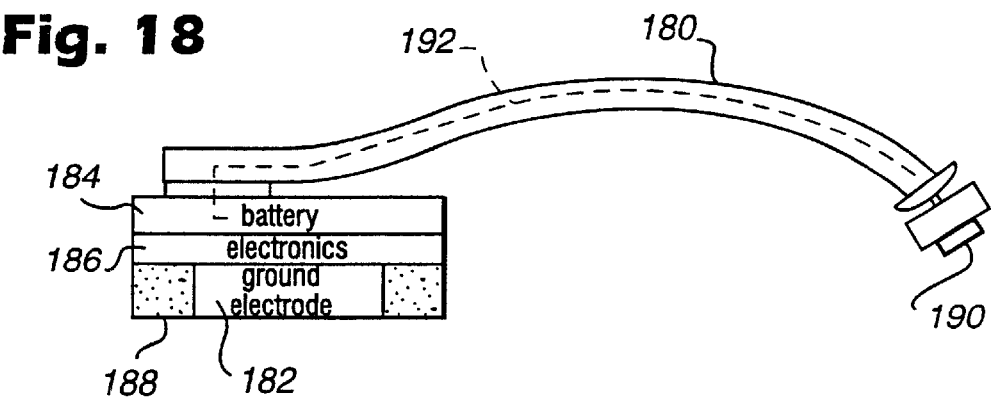
FIG. 18 is an illustration of a hands' free electrokinetic medicament delivery device.

Referring now to FIG. 18, there is illustrated a self-contained electrokinetic medicament delivery device. In this form, however, the ground electrode and the active electrode are separated one from the other by a malleable or tensionable arm 180. For example, the ground electrode 182 may be provided in a housing also containing the battery 184 and electronics 186. The ground electrode 182 may be surrounded by an adhesive 188 for adhering the ground electrode to a site on an individual directly adjacent a treatment site. The active electrode 190 is connected to the battery and electronics via an electrical conductor indicated by the dashed lines 192 through an arm 180. The arm may be flexed resiliently and retained in its flexed position. In utilizing the device of FIG. 18, the ground electrode is adhered to the individual's skin adjacent a treatment site by the adhesive 188. The arm 180 is then flexed resiliently to engage the active electrode 190 with the treatment site. By proper manipulation of the arm 180, the entire surface of the active electrode 190 may contact the treatment site thereby avoiding less than effective treatment. A biased gimbal or pivotal connection between the arm 180 and the ground electrode 182 may also be employed rather than a resilient flexible arm 180. Thus, the user may apply the device and have it operate hands' free, the electronics being activated by activation of the battery as previously described.

Figure 19:
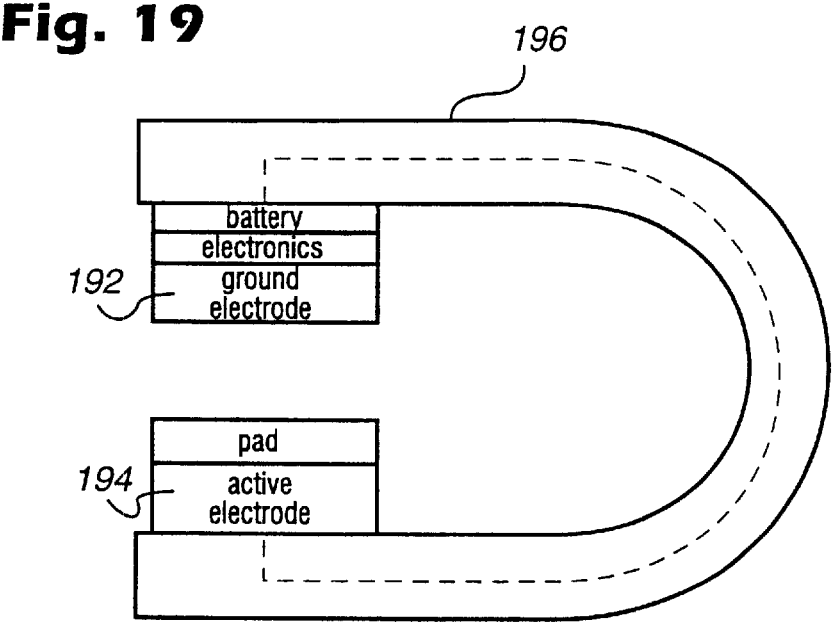
FIG. 19 is a schematic illustration of a still further hands' free electrokinetic delivery device according to the present invention.

Referring now to FIG. 19, a similar type of hands' free electrokinetic medicament delivery device is illustrated in the form of an U-shaped clip. The ground and active electrodes 192, 194 are placed at opposite distal ends of a clip 196, preferably a spring clip. By placing the electrodes on the inside of the clip, the clip may be applied to gently grip the treatment site, employing the tension of the clip to retain the clip on the treatment site whereby hands' free delivery of the medicament can be accomplished. The fully disposable U-shaped clip may have a built in unit dose applicator or may be reusable if fitted out for use with disposable applicators.

Figure 20:
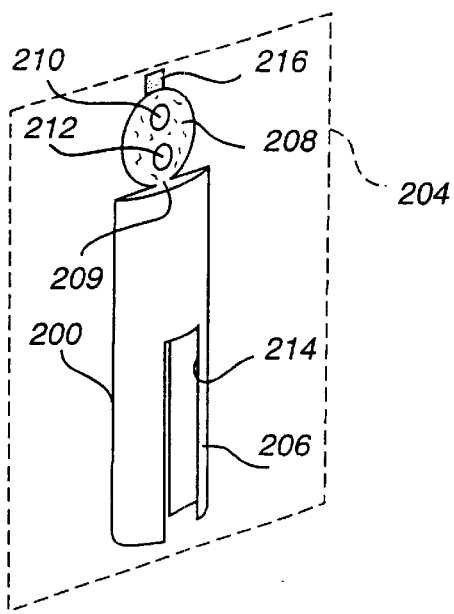
FIG. 20 is a perspective view of a further form of an applicator, illustrated with its packaging, for use with an electrokinetic delivery device.
Figure 22:
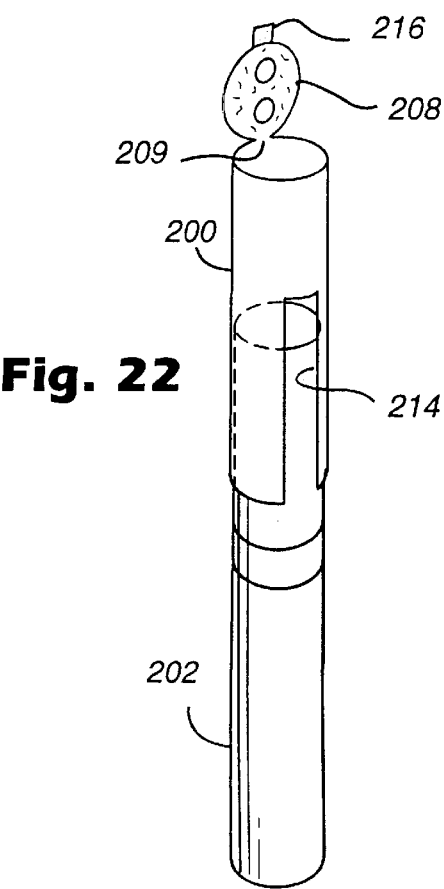
FIG. 22 is a schematic illustration of the applicator of FIGS. 20 and 21 applied to the electrokinetic device.
Figure 23:
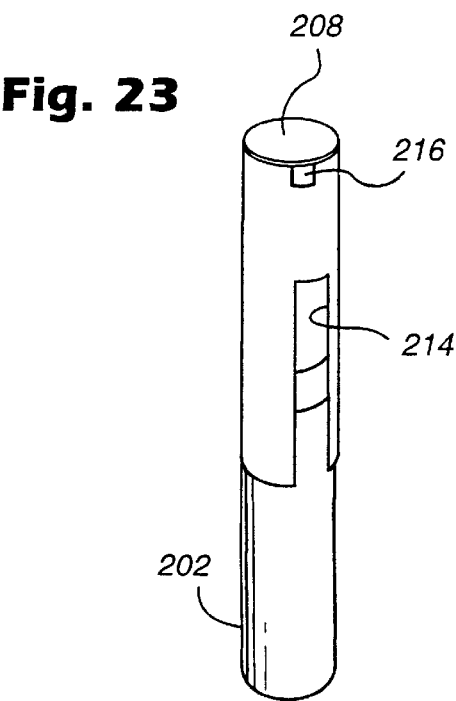
FIG. 23 is a perspective view of the device with the applicator applied ready for use.

Referring now to FIG. 20, there is illustrated a further form of an applicator 200 for use with an electrokinetic delivery device 202 (FIGS. 22 and 23) illustrated in a flat configuration and within packaging 204, for example, a plastic sealed package. Applicator 200 includes a flattened sleeve 206 open at its opposite ends and having an applicator pad 208 forming part of the sleeve and projecting from one end of the sleeve and along an edge thereof. Preferably, the applicator pad 208 is circular in form, for reasons which will become apparent and is hinged to sleeve 200 along a hinge line 209. The pad 208 is preferably a porous open cellular material through which the medicament may be transported to the treatment site. As in prior embodiments, the pad 208 may contain the medicament within the pad within the interstices of the open cellular material or the medicament may be encapsulated within rupturable capsules 210, similarly as illustrated with respect to FIGS. 7 and 8. A further alternative provides a pad without medicament, the medicament, and hydration material, if necessary, being applied to the pad by the user at the time the user employs the device to electrokinetically deliver the medicament to the treatment site. The pad 208 may additionally contain hydration material in a hydration capsule 212 similarly as illustrated in FIG. 8 in the event the medicament is not per se electrokinetically transportable.

As illustrated, the sleeve 206 is preferably formed of a fabric material similarly as the material of substrate 42. Other suitable materials may be employed forming all or part of the sleeve, i.e., the substrate of any of the applicators disclosed herein may include, polyethylene, paper, cotton, ceramic, silicone rubber, polyurethane, vinyl, polytetrafluoroethlene and other plastics. A suitable barrier may be disposed between the pad 208 and the sleeve 206 to prevent migration of the medicament onto the sleeve or migration of any electrically conductive material such as hydrogel as noted below from the sleeve 206 onto the pad 208. Opposite sides of the sleeve 200 may have cutouts 214 which open through the end of sleeve 206 opposite the pad 208 or which may be completely enclosed cutouts. Particularly, the cutouts 214 lie at circumferential positions about the sleeve 206 corresponding to the axial and circumferential positions of the tactile electrode, for example, electrode 30 as illustrated in FIG. 1. Additionally, a tab 216, preferably having a pressure sensitive adhesive on one face, projects from the pad 208 opposite from its connection with the sleeve 206.

To use the applicator 200 in conjunction with the electrokinetic delivery device 202, the packaging 204 is removed from the applicator 200. Where the medicament is encapsulated, the pad may be compressed between the individual's fingers to rupture the capsule 210 and hence spread the medicament into the interstices of the pad. Where the medicament is not per se capable of electrokinetic transport, the hydration capsule 212 is likewise ruptured to mix the medicament and hydration material such that upon application of electric current, the medicament may be transported to the treatment site. If, of course, the medicament has previously been applied to the pad, the user need not compress the pad. Alternatively, if the pad contains no medicament, the user may apply the medicament to the pad and hydration material, e.g., water or a trace saline solution, if necessary.

Figure 21:
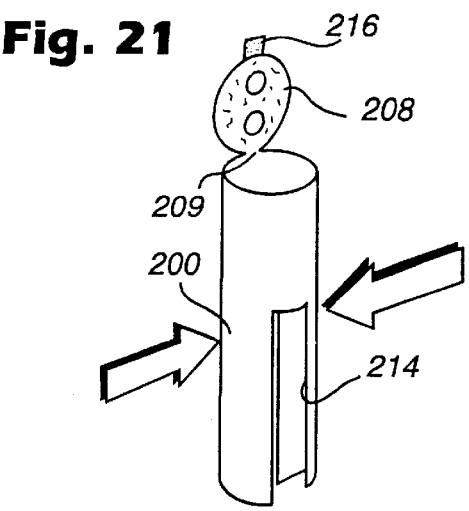
FIG. 21 is a view of the applicator of FIG. 20 without its packaging.

As illustrated in FIG. 21, pressure applied in the direction of the illustrated arrows will form the flat applicator sleeve 206 into a cylinder for reception about the end of the electrokinetic delivery device mounting the active electrode, for example, the device illustrated in FIG. 1. Upon application of sleeve 206 to the device 202, the cutouts 214 are aligned with the tactile electrode along the sides of the device 202. Additionally, the pad 208 is folded over the active electrode at the end of the device 202 and the adhesive tab secures the pad 208 in contact with the active electrode. The user may then grasp the device 202 with the user's fingers pressed against the tactile electrode of the device 202 to complete the electrical circuit, as previously described. It will be appreciated that the sleeve 206 may have, instead of cutouts 214, areas impregnated with hydrogel to facilitate electrical contact between the individual's fingers and the tactile electrode of the electrokinetic delivery device. In any embodiment, auxiliary hydration material, e.g., water may be employed. The sleeve may also contain magnetic switch activation material. After application of the device illustrated in FIG. 23 to the treatment site, the user removes the applicator 200 from the end of the device 202 and discards the applicator. The device 202 remains for subsequent use with a similar applicator or other applicators disclosed herein.

The above mechanisms may be monopolar or multi-channel (as in U.S. Pat. No. 5,160, 316, now U.S. Pat. No. Re. 36,626, incorporated herein by reference), or hybrid multi-channel in nature. By hybrid multi-channel it is meant that only one current driver is employed while more than one current limiter is employed to a corresponding number of two or more current distributive channels. A potential problem which may possibly be encountered with hand-held, electrokinetic devices, e.g., iontophoretic devices, is non-uniformity in contact pressure between the treatment surface and the active electrode surface. For a self-medicating patient using a probe-type iontophoretic device, if the probe is accidentally held at an oblique angle, non-uniform contact pressure occurs. In the small area where the contact pressure is high, the local electric resistance is low and therefore more current flows in this small area. The resulting current concentration not only prevents a uniform delivery of medicament but also can cause discomfort and even burns due to a high local current density. This detrimental occurrence can be prevented (for example, by using a multi-channel design (segmented electrode). As the contact pressure becomes uneven, the resistance of each channel or segment varies. For small changes in contact pressure and resistance, the current flowing in each channel remains constant due to servo control. However, the bias potential or voltage of each channel will change. For an area with higher contact pressure, and therefore lower resistance, the bias potential will decrease. Based on this decrease in bias potential, an early warning signal for uneven probe placement can be generated and transmitted to the patient for readjustment. If this warning is ignored, and the pressure concentration deteriorates further, some channel will reach its maximum bias potential limit and the current and the concomitant medicament delivery will decrease from the pre-set level. For the channels where the contact pressure is high and resistance is low, the current remains constant (due to servo control of the current) in spite of the reduction in resistance. This is one of the benefits of a multi-channel system where current density remains unchanged under each segmented electrode. The non-uniform contact pressure can still cause global non-uniform medicament delivery but not burns.

Figure 24:
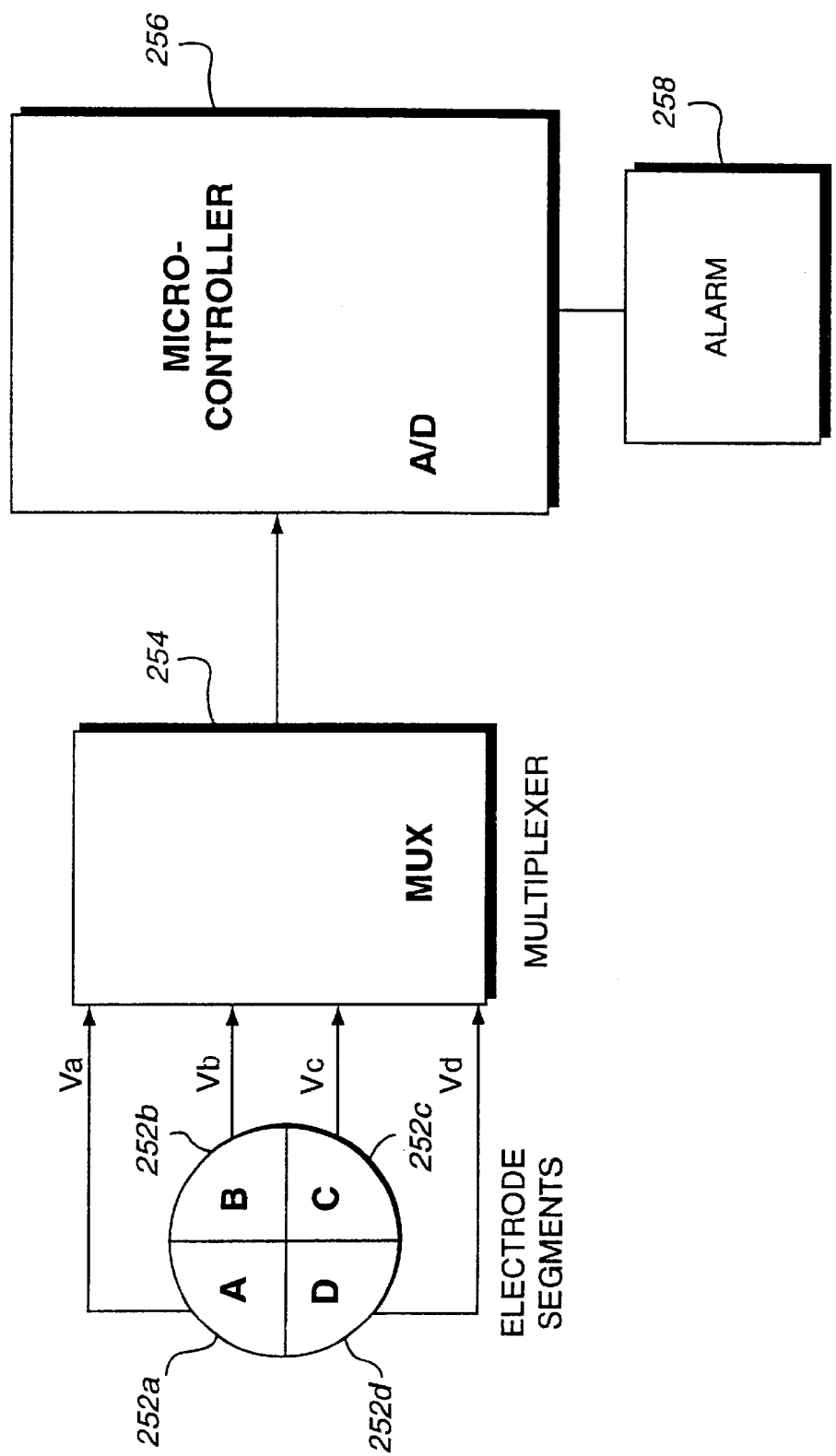
FIG. 24 is a schematic representation of an alarm system for misplacement of the probe.

An example of how the presence of non-uniform contact pressure can be detected is illustrated in FIG. 24. For ease of explanation, assume that the treatment electrode is divided into four segments 25a–d as shown in FIG. 24. Treatment currents in equal amounts, flow to electrode segments 252a–d, respectively. The current components are maintained by separate servo control loops to remain constant, irrespective of the skin and medicament conductivity, by varying the bias potential of each electrode segment. Under normal conditions in which the contact pressure is uniform, the bias potentials, Va, Vb, Vc and Vd for respective segments are substantially equal.

As shown in FIG. 24, the bias potential of each segment is connected to an analog multiplexer 254, the output of which is, in turn, connected to an analog-to-digital (A-to-D) channel of a micro-controller 256. Micro-controller 256 is an IC including a microprocessor core with digital inputs, outputs, A-to-D converter, timer, and other functional elements. The microprocessor can be programmed to conduct many diverse tasks. It can also be programmed, for example, to periodically measure and compare the bias potential of each electrode segment. If, for example, Va and Vb are found to be greater than Vc and Vd by a predetermined margin, the electrokinetic probe may be determined to be tilted downward by the patient such that the contact pressure is higher under segments C and D, and lower under segments A and B. The micro-controller can cause an alarm 258 to output an aural and/or visual alarm when the non-uniformity in contact pressure (as determined from the bias potentials) exceeds some predetermined value. Instead of using a micro-controller, the non-uniform pressure detection can also be accomplished by using discrete analog circuitry with operational amplifiers, comparators etc.

Fungal infestations of skin and its appendages are also quite common and multiple therapies are available. The infections afflict age groups from childhood to late adulthood and the aged and immune suppressed population. The infections may include, for example, diaper rash, athlete's foot or jock itch and, in children, ringworm and other dermatophytosis. The current treatment of such infections involve anti-fungal agents applied topically. In healthy patients, the topical treatment works, although sometimes frustrating in its response time and chances for recurrence.

Fungal infections of the nail bed are more refractory to standard management. These frequently distort the nails both on the feet and hand and commonly occur in people working in gardens. These infections create deformity of the nails and patients frequently ask for treatment. Unfortunately, the current treatment involves systemic drugs that have significant liver toxicity as well as side effects. Many patients fail to undergo the typical eight weeks of treatment required to control such infections.

As described herein, the present invention offers a more rapid resolution of topical infections and more effective non-systemic treatment of the more refractory nail infections. As in the prior embodiments, the treatment method and apparatus for fungal infestation employs an electrokinetic, e.g., iontophoretic transport mechanism including electronics to drive the medicament into the infected (treatment) site to ultimately prevent the fungus from replicating. There are numerous medicaments available on the market for this purpose. In addition, there are several non-pharmaceutical level agents that may have a significant benefit to the treatment of fungal infections.

Figure 25:
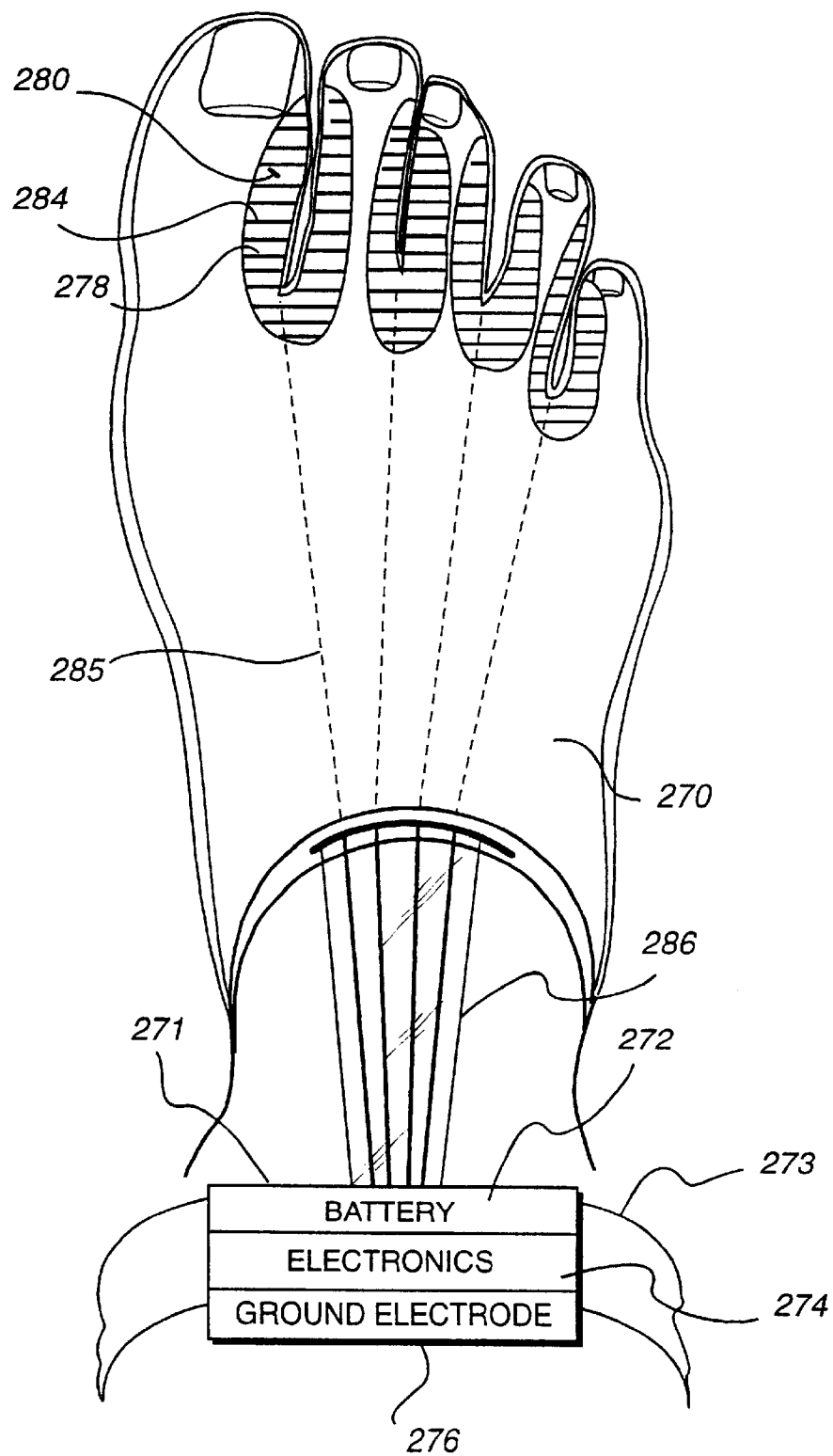
FIG. 25 is a schematic illustration of an electrokinetic applicator in the form of a sock for treatment of fungal infestations between the toes.

Referring to FIG. 25, there is illustrated an applicator 270 for the treatment of athlete's foot, e.g., where fungal infestation occurs between the toes. The applicator 270 is in the form of a flexible elastic sock electrode with an electronics package 271 containing a battery 272, electronics 274, ground electrode 276 and active electrodes 278 in registration with fungal infested areas between the individual's toes. The package 271 is strapped about the individual's ankle by a strap 273. Discrete medicament-carrying pads 280 are shaped to extend between the toes along the interior potion of the toe region of the sock. Individual branch wires 284 overlying the pads 280 and with an electrically insulative covering, not shown, are coupled to the electronics package by conductive wire leads 285 disposed in an insulative protective ribbon 286. By wearing the sock, e.g., one to two hours, and completing the circuit between each active electrode 284 and the ground electrode 276 through the individual's ankle, a single treatment is sufficient to drive the anti-fungal medication carried by the pads 280 into the infected area between the toes to completely resolve the fungal infestation. It will be appreciated that the pads may form an integral part of the elastic sock 270 preferably along the inside portion of the toe region. The medicament is preferably pre-supplied within the pads, e.g., encapsulated and with or without hydration material as in prior embodiments hereof. The sock 270 may also be disposable with the electronics package 271 or the electronic package may be disconnected and reconnected to one or more additional socks as needed for applying additional medicament at the appropriate treatment intervals.

Figure 26:
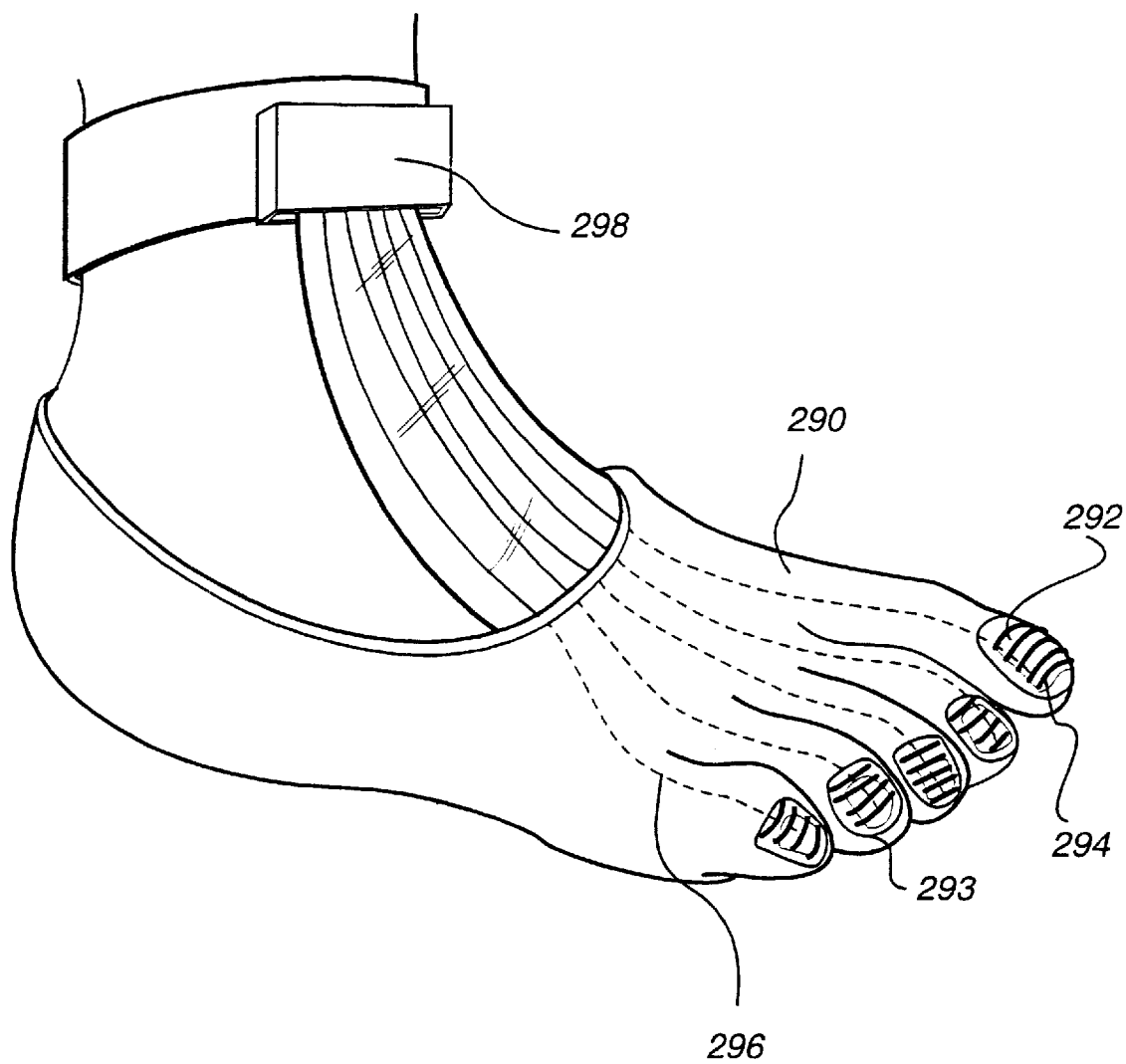
FIG. 26 is a view similar to FIG. 25 illustrating an electrokinetic applicator for treatment of a nail bed fungal infestation.

A similar arrangement is illustrated in FIG. 26 for electrokinetic application of medicaments to toenail fungal beds. In this form, the elastic sock 290 includes active electrode portions 292 overlying a pad 293 containing the anti-fungal agent in the region of the sock overlying the individual toenails. Each active electrode portion 292 may comprise short individual lead wires 294 coupled via individual leads 296 to an electronics package 298 similar to the package described and illustrated with respect to FIG. 25. Thus, electrokinetic delivery of the medicament to the nail beds of the toes is provided upon completion of the circuit through the active electrodes 294 and ground electrode in the electronics package 298 through the ankle of the individual. This treatment requires prolonged and overnight wear of the sock electrode and may involve a plurality of treatments, for example, three treatments with a spacing of about two or three days.

Referring now to FIGS. 27 and 28, there is illustrated an applicator for the treatment of fingernail fungal beds. In this form, an applicator body 300 may be generally hemispherical in shape and is preferably formed of a resiliently elastic material. In the arcuate surface of the hemispherically-shaped body 300, there is provided one or more fingerholes 302 into which the individual's fingernails may be received, e.g., up to about the first finger joint. Thus, five fingerholes 302 can be provided at various positions about the body 300 consistent with the anatomical orientation of an individual's bent fingers when his/her hand rests on the arcuate upper surface of the body 300 enabling the fingertips to be received in the openings 302.

As best illustrated in FIG. 28, the body 300 includes an active electrode 304 in each of the openings 302 at a location in registration with, i.e., opposite, the fingernail of the individual's finger when received in the hole. A medicament-containing porous pad, for example, in the form of a thimble 306, preferably pre-supplied with medicament or having encapsulated medicament along a forward edge thereof is provided. Alternatively, the individual user may apply the medicament to the thimble pad portion upon use. The thimble 306 may also contain a resilient elastic material 308, for example, sponge material, such that upon placing the thimble about the individual's fingertip and the fingertip including thimble 306 in the hole 302, the sponge material 308 biases the individual's nail forwardly into contact with the forwardmost pad portion of the thimble to make electrical contact with the active electrode 304. As in the prior embodiments, hydrating material may also be supplied integrally with the thimble, for example, in the form of encapsulated hydration material or the individual may hydrate the medicament in the thimble pad portion upon use.

As illustrated in FIG. 28, the ground electrode 310 is provided along an arcuate surface of the body 300 such that when the individual lays his/her hand over the arcuate portion of the body 300, the palm of the hand rests against ground electrode 310 with the finger or fingers in the holes 302 bearing against the pad 306 and active electrodes 304. It will be appreciated that each hole 302 has an active electrode 304 associated with that hole. The active and ground electrodes are coupled to the electronics 312 which, in turn, is coupled to a power source 314 integral with body 300. It will be appreciated that the body 300 may have other shapes, for example, an elastic spherical shape, such that the individual can carry the electrokinetic delivery device in his/her hand for the duration of the treatment period. Alternatively, as illustrated, the body 300 may have a flat undersurface enabling the individual to rest his/her hand on the upper arcuate surface of the body 300 with body 300 supported, for example, on a desk or table.

As will be appreciated from the above description, a variety of active electrodes can be designed for size and contour for application to various parts of the human body. For example, electrodes can be woven into undergarments to alleviate refractory infestation in the inguinal area, commonly described as jock itch. Moreover, applicators such as the sock electrodes described, are disposable items with prescribed medication pre-supplied for specific application.

Figure 29:
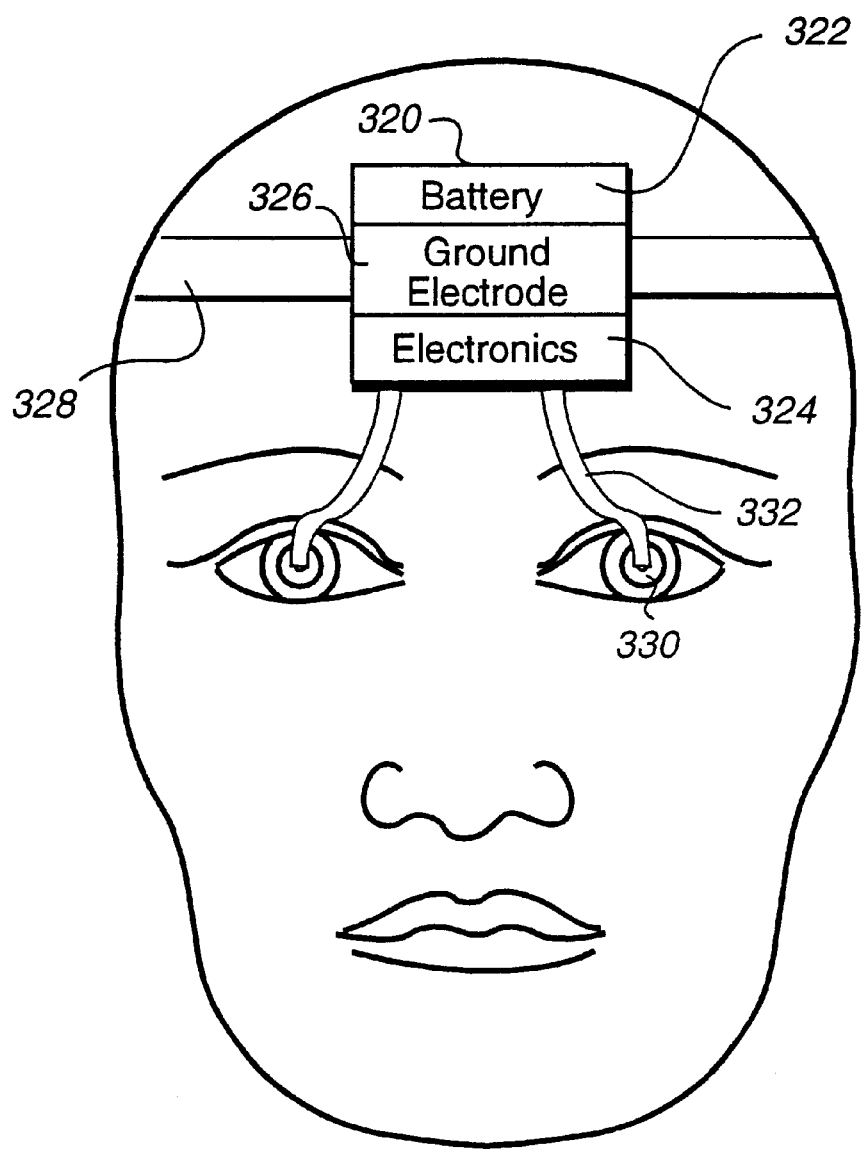
FIG. 29 is a schematic representation of a device for electrokinetic ocular treatment.
Figure 30:
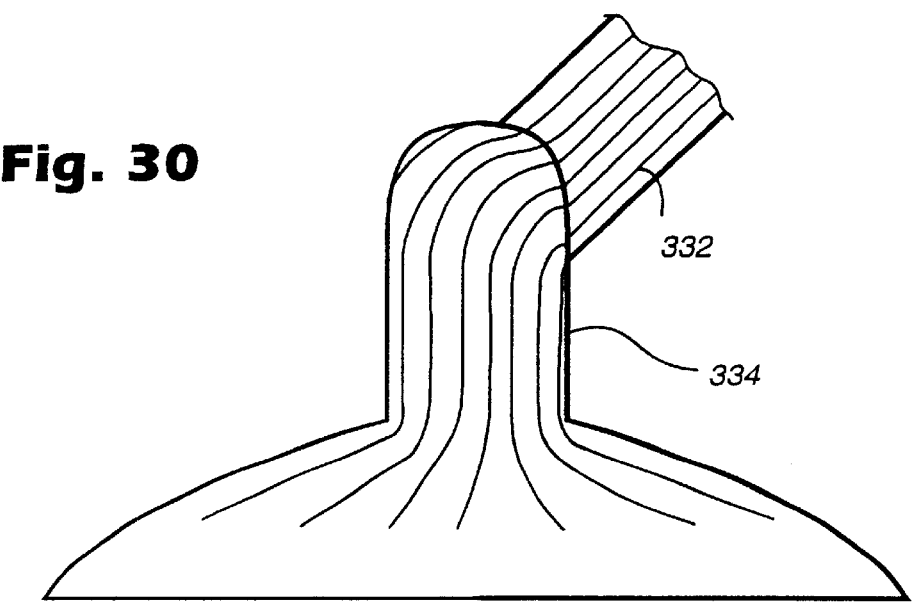
FIG. 30 is a side elevational view of an ocular applicator according to this aspect of the invention.
Figure 31:
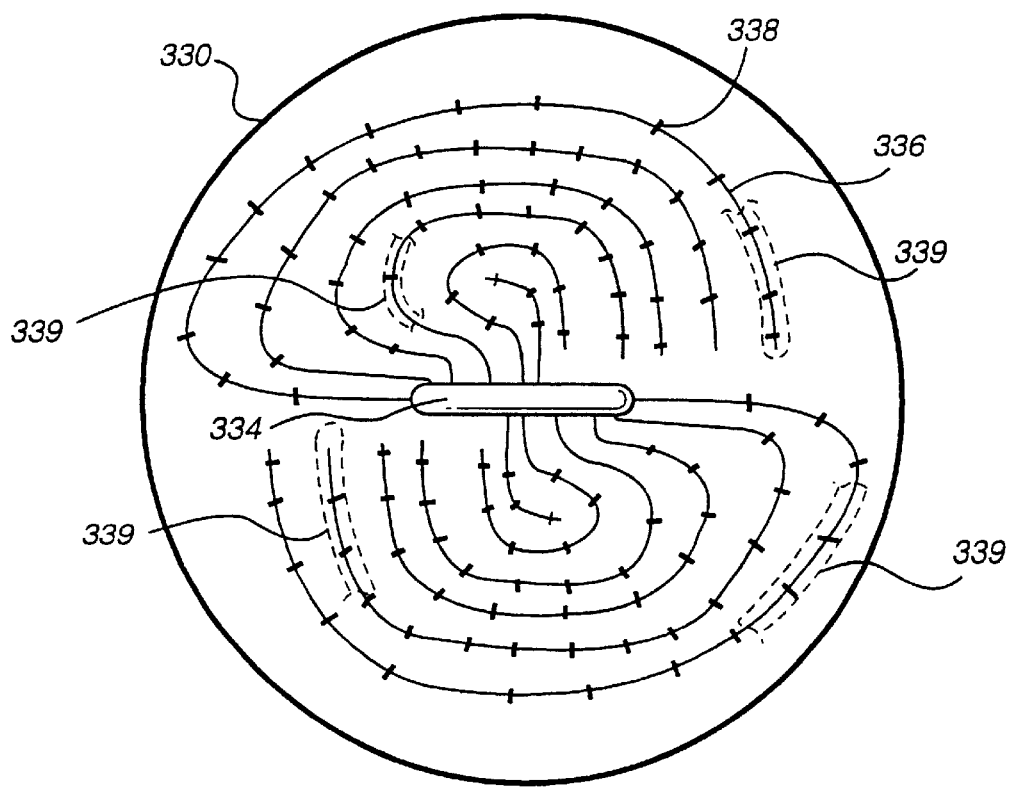
FIG. 31 is a planar view of the ocular applicator illustrating the multi-channel conductors.

Referring now to the embodiment hereof illustrated in FIGS. 29–31, various medicaments may be electrokinetically applied in an ocular application similar to and worn like a contact lens. For example, as illustrated in FIG. 29, there is provided an electronics package 320 comprised of a battery 322, electronics 324 and a ground electrode 326 carried by a strap 328 designed to envelope the individual's head releasably securing the electronics package 320 on the forehead with the ground electrode engaging the individual's forehead. Contrary to the preceding embodiment, the mechanism of the electrokinetic delivery may be a multi-channel electrode as described in U.S. Pat. No. 5,160,316, now U.S. Pat. No. Re. 36,626, incorporated herein by reference. While delivery of medicament is illustrated as being applied to both eyes simultaneously, it will be appreciated that the electrokinetic delivery system hereof can be applied to only one eye.

As illustrated, the electronics of the package 320 are coupled to an applicator electrode 330 for each eye via a ribbon cable connector 332. The applicator electrodes 330 are each in the form of a concave-convex matrix formed of electrodispersive material sufficiently flexible to fit and overlie the various contours of individual eyes. Each matrix is similar to a contact lens. Applicator electrode 330 includes a combined handle and connector 334 which projects from the convex side of the applicator electrode 330, facilitating a finger grip for the contact electrode 330 and an electrical connection for the ribbon connector 332. The individual lead wires in the ribbon connector 332 are continued through the combined handle and connector 334 into the electrode 330. As illustrated in FIG. 31, these individual conductors or lead wires 336 extend from the combined handle and connector 334, preferably in semi-circular patterns along opposite halves of the contact electrode 330. Each of the conductors 336 has a plurality of short lead wires or supplemental conductors 338 at spaced positions along each connector 336 to provide increased contact area, i.e., to further distribute the electrical current flow along the surface of the eye. Each of the lead wires or connectors 336 has a discrete pad 339 associated with it for carrying the medicament and which medicament is electrokinetically driven into the eye upon completion of the electrical circuit between the applicator electrode 330, the eye, the individual's skin between the active and ground electrodes, and the ground electrode 326.

As noted in the aforementioned patent, the lead wires 336 in each contact electrode 330 may be electrically driven simultaneously or in sequential multiplex fashion. With the current in each connector 336 being limited, for example, within the range previously discussed, current tunneling or current flow along the path of least resistance is substantially eliminated. For delivering medicaments, the ocular electrokinetic delivery system described herein is preferably worn by an individual over a period of time, for example, up to an hour, with the multi-channel driver electrokinetically delivering the medicament into the cornea. Further, the contour of the eye can be reshaped by delivering agents that retain water which would swell the conjunctiva in specific sites of the eye. By applying differential levels of power and agent delivery through use of a multi-channel system, the refraction of light can be modified by altering the shape of the eye.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. An electrokinetic delivery system for personal use in self-administration of a medicament to a treatment site on an individual, comprising:

a device for releasable securement to an individual's finger and shaped in part to conform to at least a portion of the individual's finger;

at least one of an electrically conductive medicament or a medicament with an electrically conductive carrier therefor;

a retainer for releasably securing the device to the individual's finger;

a self-contained power source carried by said device;

a first electrode carried by said device adjacent a distal end portion thereof and adjacent the tip of the individual's finger upon retention of the device on the individual's finger, said first electrode being in electrical contact with said power source;

a second electrode carried by said device for electrical contact with a portion of the individual's finger, said second electrode being in electrical contact with said power source whereby, upon application of said first electrode to a treatment site with said at least one medicament interposed between the first electrode and the treatment site and completion of an electrical circuit through the first electrode, the at least one medicament, the treatment site, the individual's body, said second electrode and said power source, said device causes an electrical current to flow for electrokinetically driving the at least one medicament into the treatment site.

2. The system according to claim 1 wherein delivery of the at least one medicament to the treatment site at least aids in treatment or prevention of diseases or other abnormal or cosmetic conditions of skin or mucocutaneous membrane.

3. The system according to claim 1 wherein delivery of the at least one medicament to the treatment site at least aids in treatment or prevention of infection.

4. The system according to claim 1 wherein said at least one medicament to the treatment site is at least intended to treat or prevent bacterial infection of skin.

5. The system according to claim 1 wherein said at least one medicament is at least intended to treat or prevent viral infection of skin.

6. The system according to claim 1 wherein said at least one medicament is at least intended to treat or prevent microbial infection of skin.

7. The system according to claim 1 wherein said at least one medicament is at least intended to stimulate hair growth.

8. The system according to claim 1 wherein said at least one medicament is at least intended to treat a wound.

9. The system according to claim 1 wherein said at least one medicament is at least intended to treat acne.

10. The system according to claim 1 wherein said at least one medicament is at least intended to treat psoriasis.

11. The system according to claim 1 wherein said at least one medicament is at least intended to treat eczema or contact or atopic dermatitis.

12. The system according to claim 1 wherein said at least one medicament is at least intended to treat pruritis, dry skin, or keratosis.

13. The system according to claim 1 wherein said at least one medicament is at least intended to treat actinic keratoses.

14. The system according to claim 1 wherein said at least one medicament is at least intended to treat spider veins.

15. The system according to claim 1 wherein delivery of the at least one medicament is at least intended to treat skin cancer.

16. The system according to claim 1 wherein delivery of the at least one medicament to the treatment site at least relieves pain.

17. The system according to claim 1 wherein said at least one medicament is at least intended to treat a herpetic symptom.

18. The system according to claim 1 wherein said at least one medicament is at least intended to treat post-herpetic neuralgia.

19. The system according to claim 1 wherein said at least one medicament is an antiviral.

20. The system according to claim 1 wherein said at least one medicament is an anesthetic.

21. The system according to claim 1 wherein said at least one medicament is at least intended to treat an inflammatory condition.

22. The system according to claim 1 wherein said at least one medicament is dexamethasone.

23. The system according to claim 1 wherein said at least one medicament comprises at least one anesthetic selected from the group consisting of lidocaine, xylocaine, prontocaine, prilocaine, fetanyl, remifentanil, sufentanil, alfentanil, novocaine, procaine, morphine HCI and EMLA.

24. The system according to claim 1 wherein said at least one medicament comprises an anti-proliferative agent or an anti-angiogenic agent.

25. The system according to claim 1 wherein said at least one medicament comprises at least one chemical selected from the group consisting of 5-fluorouracil, cisplatin, Efudex, soviudine and thalidomide.

26. The system according to claim 1 wherein said at least one medicament is at least intended to treat a varicella zoster symptom.

27. The system according to claim 1 wherein said at least one medicament comprises acyclovir.

28. The system according to claim 1 wherein said at least one medicament comprises a chemical selected from the group consisting of analogs and derivatives of acyclovir.

29. The system according to claim 1 wherein said at least one medicament comprises at least penciclovir or famciclovir.

30. The system according to claim 1 wherein said at least one medicament comprises a behenyl alcohol.

31. The system according to claim 1 wherein said at least one medicament comprises n-docosanol.

32. The system according to claim 1 wherein said at least one medicament comprises at least one chemical selected from the group consisting of analogs and derivatives of n-docosanol.

33. The system according to claim 1 wherein said at least one medicament comprises 5-iodo-2 deoxyuridine (IUDR).

34. The system according to claim 1 wherein said at least one medicament comprises at least one chemical selected from the group consisting of cytosine arabinoside (Ara-C), adenine arabinoside (Ara-A), adenine arabinoside monophosphate (Ara-AMP), arabinofuranosyl hypoxanthine (Ara-Hx), phosphonoacetic acid (PAA), thymine arabinoside (Ara-T), 5'-amino-2', 5'-dideoxy-5-iodouridine (AIU), 1-beta-D-arabinofuranosyl-E-5-(2-bromovinyl)uracil (BV-ara-U), 1-beta-D-arabinofuranosyl-E-5(2-chlorovinyl)uracil (CV-ara-U), halogenated deoxytidines BrCdR and ICdR, and bromovinyldeoxyuridine (BVDU).

35. The system according to claim 1 wherein said at least one medicament comprises an antiviral and an anesthetic.

36. The system according to claim 1 wherein said at least one medicament is at least intended to treat an infection by a human papilloma virus.

37. The system according to claim 1 wherein said at least one medicament comprises at least one chemical selected from the group consisting of Imiquimod, sodium salicylate, tretinion, benzoyl peroxide, bleomycin, interferons, Podocon-25, Wart Off and Compound W.

38. The system according to claim 1 wherein said at least one medicament comprises an antibiotic.

39. The system according to claim 1 wherein said at least one medicament comprises at least one chemical selected from the group consisting of finasteride, minoxidil, antidihydrotestosterones and antidihydroestrogens.

40. The system according to claim 1 wherein said at least one medicament comprises at least a steroidal or non-steroidal anti-inflammatory drug (NSAID).

41. The system according to claim 1 wherein said at least one medicament comprises at least one chemical or biologic selected from the group consisting of benzamycin, benzoyl peroxide, cleocin, T-Stat, Clearasil, Benzac, Accutane, tazarotene, adapalene, azelaic acid and erythromycin.

42. The system according to claim 1 wherein said at least one medicament comprises at least one chemical or biologic selected from the group consisting of anesthetics, analgesics, and other desensitizing agents.

43. The system according to claim 1 wherein said at least one medicament comprises at least one chemical or biologic selected from the group consisting of vasodilators, antihistamines, antimetabolites, immunosuppressives, and antineoplastic agents.

44. The system according to claim 1 wherein said at least one medicament comprises at least one chemical or biologic selected from the group consisting of antiandrogens, beta blockers, beta-adrenergic antagonists, catecholamines, modulators of collagen deposition, and sympathomimetics.

45. The system according to claim 1 wherein said first electrode includes a multi-channel electrode, each electrode channel being electrically driven in a current isolated fashion through a corresponding plurality of individual current loops with each channel receiving substantially the same current level.

46. The system according to claim 1 including a current driver, said first electrode including a plurality of current distributive channels and a plurality of current limiters coupled between said driver and said channels to provide substantially the same current level in each said channel.

47. The system according to claim 1 including a vibratory element carried by said device and electrically coupled to said power source for inducing ultrasonic vibration into the treatment site.

48. The system according to claim 1 wherein said device is disposable after one-time usage.

49. The system according to claim 1 wherein said medicament comprises an anti-fungal.

50. The system according to claim 1 wherein said at least one medicament aids in the treatment or prevention of a disease condition caused by or suspected to be caused by a fungus.

* * * * *